US007285649B2

(12) United States Patent
Akita et al.

(10) Patent No.: US 7,285,649 B2
(45) Date of Patent: Oct. 23, 2007

(54) ISOLATED NUCLEIC ACIDS, VECTORS AND HOST CELLS ENCODING ERBB3 ANTIBODIES

(75) Inventors: Robert Akita, Hayward, CA (US); Mark Sliwkowski, San Carlos, CA (US)

(73) Assignee: Genentech, Inc., South San Francisco, CA (US)

( * ) Notice: Subject to any disclaimer, the term of this patent is extended or adjusted under 35 U.S.C. 154(b) by 868 days.

(21) Appl. No.: 09/825,584

(22) Filed: Apr. 4, 2001

(65) Prior Publication Data

US 2002/0064805 A1    May 30, 2002

Related U.S. Application Data

(60) Division of application No. 09/316,981, filed on May 24, 1999, now abandoned, which is a continuation of application No. 08/827,009, filed on Mar. 25, 1997, now Pat. No. 5,968,511.

(60) Provisional application No. 60/046,850, filed on Mar. 27, 1996.

(51) Int. Cl.
*C12N 15/11* (2006.01)
(52) U.S. Cl. ............... 536/23.1; 435/91.1; 435/325
(58) Field of Classification Search ............... 536/23.1; 435/91.1, 325
See application file for complete search history.

(56) References Cited

U.S. PATENT DOCUMENTS

| 4,816,397 | A | * | 3/1989 | Boss et al. |
| 4,816,567 | A | * | 3/1989 | Cabilly et al. |
| 4,975,278 | A | | 12/1990 | Senter et al. |
| 5,183,884 | A | | 2/1993 | Kraus et al. |
| 5,258,498 | A | * | 11/1993 | Huston et al. |
| 5,480,968 | A | | 1/1996 | Kraus et al. |
| 5,618,920 | A | * | 4/1997 | Robinson et al. |
| 5,783,186 | A | | 7/1998 | Arakawa et al. |
| 5,783,404 | A | | 7/1998 | Koski |
| 5,820,859 | A | | 10/1998 | Kraus et al. |
| 5,916,755 | A | | 6/1999 | Kraus et al. |
| 5,968,511 | A | | 10/1999 | Akita et al. |

FOREIGN PATENT DOCUMENTS

| EP | 444961 | 9/1991 |
| EP | 502812 | 9/1992 |
| EP | 0599274 A1 | 6/1994 |
| WO | WO91/08214 | 6/1991 |
| WO | WO92/20798 | 11/1992 |
| WO | WO93/16185 | 8/1993 |
| WO | WO93/21319 | 10/1993 |
| WO | WO94/04679 | 3/1994 |
| WO | WO94/08007 | 4/1994 |
| WO | WO94/22478 | 10/1994 |
| WO | WO95/14776 | 6/1995 |
| WO | WO97/20858 | 6/1997 |

OTHER PUBLICATIONS

Orlandi et al (Proc. Natl. Acad. Sci. USA, 86:3833-3837, 1989).*
Ward et al (Nature 341:544-546, 1989).*
Queen et al (PNAS 1989;86:10029-33).*
Greenspan et al. (Nature Biotechnology 7: 936-937, 1999).*
Kraus et al., "Isolation and characterization of ERBB3, a third member of the ERBB/epidermal growth factor receptor family: Evidence for overexpression in a subset of human mammary tumors" *Proc. Natl. Acad. Sci. USA* 86:9193-9197 (Dec. 1989).
Lee et al., "Assignment of heregulin (HGL) to human chromosome 8p22-p11 by PCR analysis of somatic cell hybrid DNA" *Genomics* 16:790-791 (1993).
Lemoine et al., "Expression of the ERBB3 gene product in breast cancer" *Br. J. Cancer* 66:1116-1121 (1992).
Lemoine et al., "The erbB-3 gene in human pancreatic cancer" *J. Pathol.* 168:269-273 (1992).
Levi et al., "The Influence of Heregulins on Human Schwann Cell Proliferation" *J. Neuroscience* 15(2):1329-1340 (Feb. 1995).
Lewis et al., "Growth Regulation of Human Breast and Ovarian Tumor Cells by Heregulin: Evidence for the Requirement of ErbB2 as a Critical Component in Mediating Heregulin Responsiveness" *Cancer Research* 56:1457-1465 (Mar. 15, 1986).
Marchionni et al., "Glial growth factors are alternatively spliced erbB2 ligands expressed in the nervous system" *Nature* 362:312-318 (1993).
Morrissey et al., "Axon-induced mitogenesis of human Schwann cells involves heregulin and p185$^{erbB2}$" *Proc. Natl. Acad. Sci. USA* 92:1431-1435 (Feb. 1995).
Orr-Urtreger et al., "Neural expression and chromosomal mapping of Neu differentiation factor to 8p12-p21" *Proc. Natl. Acad. Sci. USA* 90:1867-1871 (1993).
Peles et al., "Isolation of the Neu/HER-2 Stimulatory Ligand: A 44 Kd Glycoprotein That Induces Differentiation of Mammary Tumor Cells" *Cell* 69(1):205-216 (1992).
Plowman et al., "Heregulin induces tyrosine phosphorylation of HER4/p180$^{erbB4}$" *Nature (Letters to Nature)* 366:473-475 (Dec. 2, 1993).
Plowman et al., "Ligand-specific activation of HER4/p180$^{erbB4}$, a fourth member of the epidermal growth factor receptor family" *Proc. Natl. Acad. Sci. USA* 90:1746-1750 (Mar. 1993).
Plowman et al., "Molecular cloning and expression of an additional epidermal growth factor receptor-related gene" *Proc. Natl. Acad. Sci.* 87:4905-4909 (1990).
Poller et al., "Production and characterization of a polyclonal antibody to the c-erbB-3 protein: examination of c-erbB-3 protein expression in adenocarcinomas" *J. Pathol.* 168(3):275-280 (1992).

(Continued)

*Primary Examiner*—Christopher H. Yaen
(74) *Attorney, Agent, or Firm*—Deirdre L. Conley; Ginger R. Dreger; Heller Ehrman LLP

(57) ABSTRACT

Antibodies are disclosed which bind to ErbB3 protein and further possess any one or more of the following properties: an ability to reduce heregulin-induced formation of an ErbB2-ErbB3 protein complex in a cell which expresses ErbB2 and ErbB3; the ability to increase the binding affinity of heregulin for ErbB3 protein; and the characteristic of reducing heregulin-induced ErbB2 activation in a cell which expresses ErbB2 and ErbB3.

7 Claims, 2 Drawing Sheets

OTHER PUBLICATIONS

Rajkumar et al., "A monoclonal antibody to the human c-erbB3 protein stimulates the anchorage-independent growth of breast cancer cell lines" *Br. J. Cancer* 70(3):459-465 (1994).

Rajkumar et al., "Expression of the c-erbB-3 protein in gastrointestinal tract tumours determined by monoclonal antibody RTJ1" *J. Pathol.* (Published erratum appears in J.Pathol.1993 Oct.;171(2):154) 170:271-278 (1993).

Ram et al., "Mitogenic Activity of Neu Differentiation Factor/Heregulin Mimics That of Epidermal Growth Factor and Insulin-Like Growth Factor-1 in Human Mammary Epithelial Cells" *J. Cellular Physiology* 163:589-596 (1995).

Sanidas et al., "Expression of the c-erbB-3 gene product in gastric cancer" *Int. J. Cancer* 54:935-940 (1993).

Slamon et al., "Human Breast Cancer: Correlation of Relapse and Survival with Amplification of the HER-2/neu Oncogene" *Science* 235:177-182 (Jan. 9, 1987).

Slamon et al., "Studies of the HER-2/neu Proto-oncogene in Human Breast and Ovarian Cancer" *Science* 244:707-712 (May 12, 1989).

Bacus et al., "Expression of the erbB-2 Family of Growth Factor Receptors and Their Ligands in Breast Cancers" *Pathology Patterns* (Suppl. 1) 102(4):S13-S24 (1994).

Falls et al., "ARIA, a protein that stimulates acetylcholine receptor synthesis, is a member of the Neu ligand family" *Cell* 72:801-815 (1993).

Fendly et al., "Characterization of Murine Monoclonal Antibodies Reactive to Either the Human Epidermal Growth Factor Receptor or HER2/neu Gene Product" *Cancer Research* 50:1550-1558 (Mar. 1, 1990).

Friess et al., "Enhanced erbB-3 Expression in Human Pancreatic Cancer Correlates with Tumor Progression" *Clinical Cancer Research* 1:1413-1420 (1995).

Griffiths et al., "Human Anti-Self Antibodies With High Specific From Phage Display Libraries" *EMBO Journal* 12(2):725-734 (1993).

Guy et al., "Insect Cell-expressed p180$^{erbB3}$ Possesses an Impaired Tyrosine Kinase Activity" *Proc. Natl. Acad. Sci. USA* 91:8132-8136 (Aug. 1994).

Holmes et al., "Identification of Heregulin, a Specific Activator of p185$^{erbB2}$" *Science* 256:1205-1210 (May 22, 1992).

Kim et al., "Epidermal growth factor-dependent association of phosphatidylinositol 3-kinase with the erbB3 gene product" *Journal of Biological Chemistry* 269(40):24747-24755 (1994).

Kraus et al., "Demonstration of ligand-dependent signaling by the erbB-3 tyrosine kinase and its constitutive activation in human breast tumor cells" *Proc. Natl. Acad. Sci.* 90:2900-2904 (1993).

Sliwkowski et al., "Coexpression of erbB2 and erbB3 Proteins Reconstitutes a High Affinity Receptor for Heregulin" *Journal of Biological Chemistry* 269(20):14661-14665 (May 20, 1994).

Wallasch et al., "Heregulin-dependent regulation of HER2/neu oncogenic signaling by heterodimerization with HER3" *EMBO Journal* 14(17):4267-4275 (1995).

Wen et al., "Neu differentiation factor: a transmembrane glycoprotein containing an EGF Domain and an Immunoglobulin Homology Unit" *Cell* 69(3):559-572 (1992).

Wen et al., "Structural and functional aspects of the multiplicity of neu differentiation factors" *Molecular & Cellular Biology* 14(3):1909-1919 (1994).

* cited by examiner

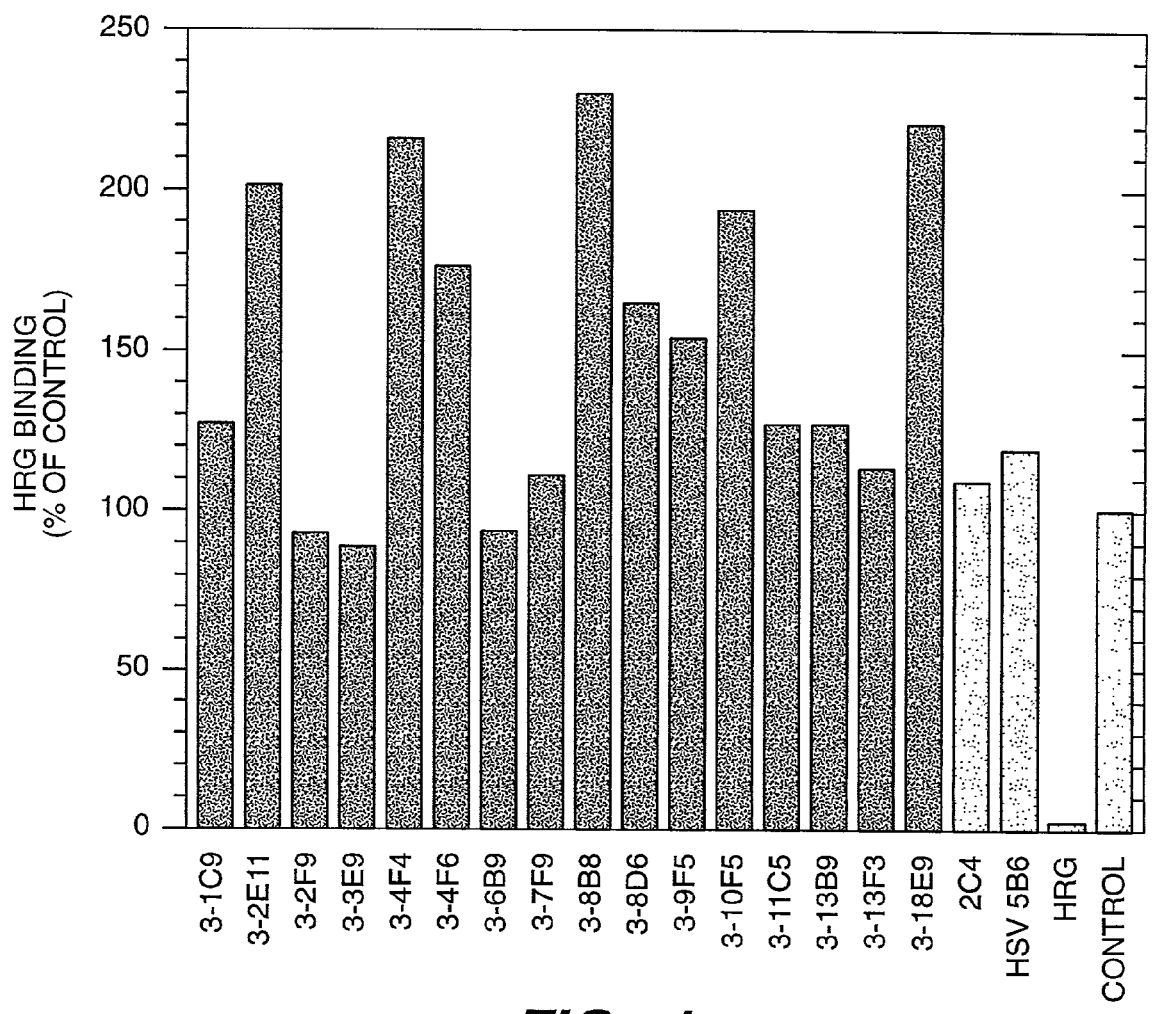
FIG._1

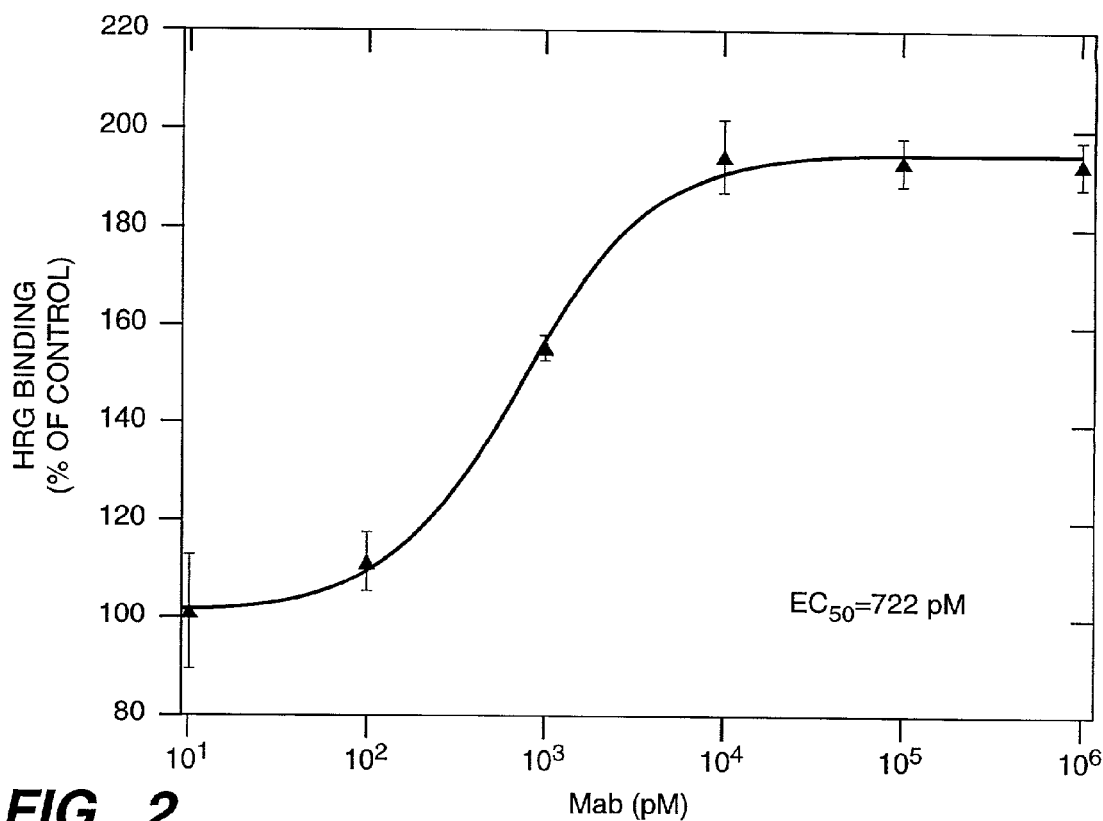
FIG._2
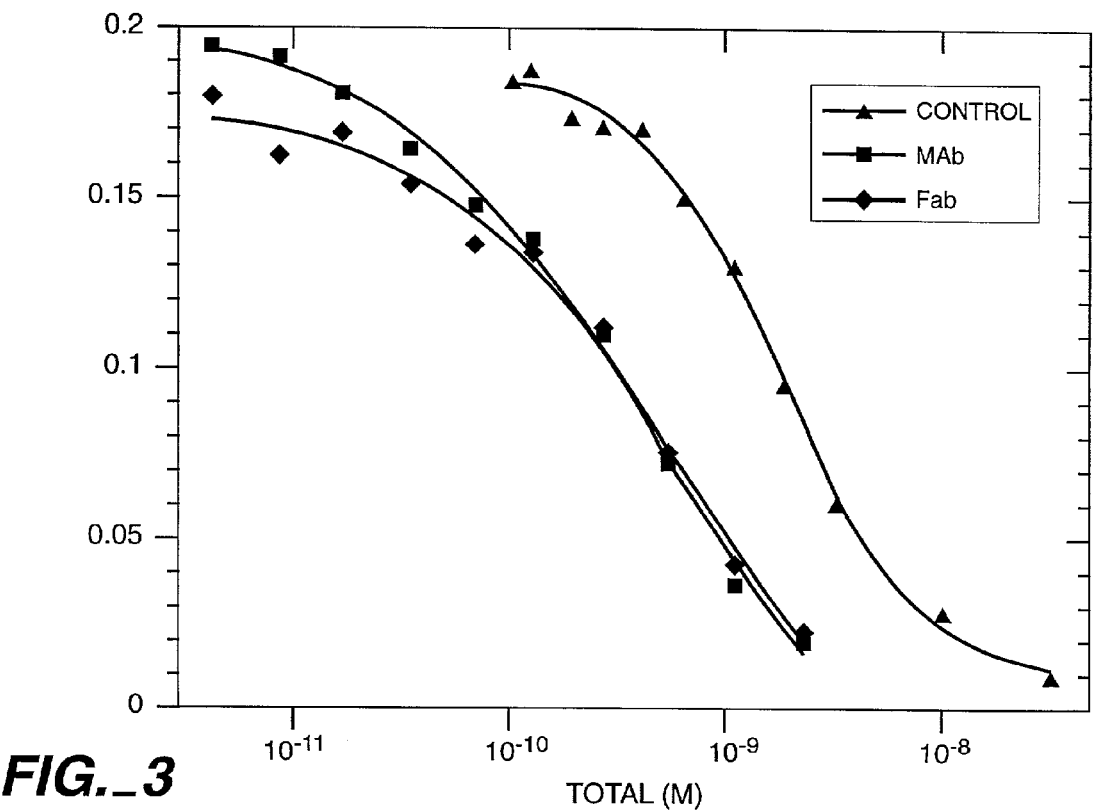
FIG._3

```
                           SEQUENCE LISTING (1) GENERAL INFORMATION:

(iii) NUMBER OF SEQUENCES: 5

(2) INFORMATION FOR SEQ ID NO: 1:

(i) SEQUENCE CHARACTERISTICS:
           (A) LENGTH: 11 amino acids
           (B) TYPE: Amino Acid
           (D) TOPOLOGY: Linear (xi) SEQUENCE DESCRIPTION: SEQ ID NO: 1:

Pro Lys Asn Ser Ser Met Ile Ser Asn Thr Pro
    1               5                   10  11

(2) INFORMATION FOR SEQ ID NO: 2:

(i) SEQUENCE CHARACTERISTICS:
           (A) LENGTH: 7 amino acids
           (B) TYPE: Amino Acid
           (D) TOPOLOGY: Linear (xi) SEQUENCE DESCRIPTION: SEQ ID NO: 2:

His Gln Ser Leu Gly Thr Gln
    1               5       7

(2) INFORMATION FOR SEQ ID NO: 3:

(i) SEQUENCE CHARACTERISTICS:
           (A) LENGTH: 8 amino acids
           (B) TYPE: Amino Acid
           (D) TOPOLOGY: Linear (xi) SEQUENCE DESCRIPTION: SEQ ID NO: 3:

His Gln Asn Leu Ser Asp Gly Lys
    1               5           8

(2) INFORMATION FOR SEQ ID NO: 4:

(i) SEQUENCE CHARACTERISTICS:
```

```
        (A) LENGTH: 8 amino acids
        (B) TYPE: Amino Acid
        (D) TOPOLOGY: Linear (xi) SEQUENCE DESCRIPTION: SEQ ID NO: 4:

His Gln Asn Ile Ser Asp Gly Lys
 1               5           8

(2) INFORMATION FOR SEQ ID NO: 5:

(i) SEQUENCE CHARACTERISTICS:
        (A) LENGTH: 8 amino acids
        (B) TYPE: Amino Acid
        (D) TOPOLOGY: Linear (xi) SEQUENCE DESCRIPTION: SEQ ID NO: 5:

Val Ile Ser Ser His Leu Gly Gln
 1               5           8
```

ISOLATED NUCLEIC ACIDS, VECTORS AND HOST CELLS ENCODING ERBB3 ANTIBODIES

This application is a divisional of U.S. application Ser. No. 09/316,981 filed May 24, 1999, now abandoned which is a continuation of U.S. application Ser. No. 08/827,009 filed Mar. 25, 1997 (now U.S. Pat. No. 5,968,511 issued Oct. 19, 1999), which is a non-provisional application filed under 37 CFR 1.53(b)(1), claiming priority under USC §119(e) to provisional Application Ser. No. 60/046,850 filed Mar. 27, 1996 (now abandoned), which applications are incorporated herein by reference.

BACKGROUND OF THE INVENTION

1. Field of the Invention

This invention relates generally to antibodies which bind the ErbB3 receptor. In particular, it relates to anti-ErbB3 antibodies which, surprisingly, increase the binding affinity of heregulin (HRG) for ErbB3 protein and/or reduce HRG-induced formation of an ErbB2-ErbB3 protein complex in a cell which expresses both these receptors and/or reduce heregulin-induced ErbB2 activation in such a cell.

2. Description of Related Art

Transduction of signals that regulate cell growth and differentiation is regulated in part by phosphorylation of various cellular proteins. Protein tyrosine kinases are enzymes that catalyze this process. Receptor protein tyrosine kinases are believed to direct cellular growth via ligand-stimulated tyrosine phosphorylation of intracellular substrates. Growth factor receptor protein tyrosine kinases of the class I subfamily include the 170 kDa epidermal growth factor receptor (EGFR) encoded by the erbB1 gene. erbB1 has been causally implicated in human malignancy. In particular, increased expression of this gene has been observed in more aggressive carcinomas of the breast, bladder, lung and stomach.

The second member of the class I subfamily, p185$^{neu}$, was originally identified as the product of the transforming gene from neuroblastomas of chemically treated rats. The neu gene (also called erbB2 and HER2) encodes a 185 kDa receptor protein tyrosine kinase. Amplification and/or over-expression of the human HER2 gene correlates with a poor prognosis in breast and ovarian cancers (Slamon et al., *Science*, 235:177-182 (1987); and Slamon et al., *Science*, 244:707-712 (1989)). Overexpression of HER2 has also been correlated with other carcinomas including carcinomas of the stomach, endometrium, salivary gland, lung, kidney, colon and bladder.

A further related gene, called erbB3 or HER3, has also been described. See U.S. Pat. Nos. 5,183,884 and 5,480,968; Plowman et al., *Proc. Natl. Acad. Sci. USA*, 87:4905-4909 (1990); Kraus et al., *Proc. Natl. Acad. Sci. USA*, 86:9193-9197 (1989); EP Pat Appln No 444,961A1; and Kraus et al., *Proc. Natl. Acad. Sci. USA*, 90:2900-2904 (1993). Kraus et al. (1989) discovered that markedly elevated levels of erbB3 mRNA were present in certain human mammary tumor cell lines indicating that erbB3, like erbB1 and erbB2, may play a role in some human malignancies. These researchers demonstrated that some human mammary tumor cell lines display significant elevation of steady-state ErbB3 tyrosine phosphorylation, further indicating that this receptor may play a role in human malignancies. Accordingly, diagnostic bioassays utilizing antibodies which bind to ErbB3 are described by Kraus et al. in U.S. Pat. Nos. 5,183,884 and 5,480,968.

The role of erbB3 in cancer has been explored by others. It has been found to be overexpressed in breast (Lemoine et al., *Br. J. Cancer*, 66:1116-1121 (1992)), gastrointestinal (Poller et al., *J. Pathol.*, 168:275-280 (1992), Rajkumer et al., *J. Pathol.*, 170:271-278 (1993), and Sanidas et al., *Int. J. Cancer*, 54:935-940 (1993)), and pancreatic cancers (Lemoine et al., *J. Pathol.*, 168:269-273 (1992), and Friess et al., *Clinical Cancer Research*, 1:1413-1420 (1995)).

ErbB3 is unique among the ErbB receptor family in that it possesses little or no intrinsic tyrosine kinase activity (Guy et al., *Proc. Natl. Acad. Sci. USA* 91:8132-8136 (1994) and Kim et al. *J. Biol. Chem.* 269:24747-55 (1994)). When ErbB3 is co-expressed with ErbB2, an active signaling complex is formed and antibodies directed against ErbB2 are capable of disrupting this complex (Sliwkowski et al., *J. Biol. Chem.*, 269(20):14661-14665 (1994)). Additionally, the affinity of ErbB3 for heregulin (HRG) is increased to a higher affinity state when co-expressed with ErbB2. See also, Levi et al., *Journal of Neuroscience* 15: 1329-1340 (1995); Morrissey et al., *Proc. Natl. Acad. Sci. USA* 92: 1431-1435 (1995); and Lewis et al., *Cancer Res.*, 56:1457-1465 (1996) with respect to the ErbB2-ErbB3 protein complex.

Rajkumar et al., *British Journal Cancer*, 70(3):459-465 (1994), developed a monoclonal antibody against ErbB3 which had an agonistic effect on the anchorage-independent growth of cell lines expressing this receptor.

The class I subfamily of growth factor receptor protein tyrosine kinases has been further extended to include the HER4/p180$^{erbB4}$ receptor. See EP Pat Appln No 599,274; Plowman et al., *Proc. Natl. Acad. Sci. USA*, 90:1746-1750 (1993); and Plowman et al., *Nature*, 366:473-475 (1993). Plowman et al. found that increased HER4 expression closely correlated with certain carcinomas of epithelial origin, including breast adenocarcinomas. Accordingly, diagnostic methods for detection of human neoplastic conditions (especially breast cancers) which evaluate HER4 expression are described in EP Pat Appln No. 599,274.

The quest for an activator of the HER2 oncogene has lead to the discovery of a family of heregulin polypeptides. These proteins appear to result from alternative splicing of a single gene which was mapped to the short arm of human chromosome 8 by Lee et al., *Genomics*, 16:790-791(1993); and Orr-Urtreger et al., *Proc. Natl. Acad. Sci. USA*, 90:1867-1871 (1993).

Holmes et al. isolated and cloned a family of polypeptide activators for the HER2 receptor which they termed heregulin-α (HRG-α), heregulin-β1 (HRG-β1), heregulin-β2 (HRG-β2), heregulin-β2-like (HRG-β2-like), and heregulin-β3 (HRG-β3). See Holmes et al., *Science*, 256:1205-1210 (1992); and WO 92/20798. The 45 kDa polypeptide, HRG-α, was purified from the conditioned medium of the MDA-MB-231 human breast cancer cell line. These researchers demonstrated the ability of the purified heregulin polypeptides to activate tyrosine phosphorylation of the HER2 receptor in MCF-7 breast tumor cells. Furthermore, the mitogenic activity of the heregulin polypeptides on SK-BR-3 cells (which express high levels of the HER2 receptor) was illustrated. Like other growth factors which belong to the EGF family, soluble HRG polypeptides appear to be derived from a membrane bound precursor (called pro-HRG) which is proteolytically processed to release the 45 kDa soluble form. These pro-HRGs lack a N-terminal signal peptide.

While heregulins are substantially identical in the first 213 amino acid residues, they are classified into two major types, α and β, based on two variant EGF-like domains which differ in their C-terminal portions. Nevertheless, these EGF-like domains are identical in the spacing of six cysteine residues contained therein. Based on an amino acid sequence comparison, Holmes et al. found that between the first and sixth cysteines in the EGF-like domain, HRGs were 45% similar to heparin-binding EGF-like growth factor (HB-EGF), 35% identical to amphiregulin (AR), 32% identical to TGF-α, and 27% identical to EGF.

The 44 kDa neu differentiation factor (NDF), which is the rat equivalent of human HRG, was first described by Peles et al., *Cell*, 69:205-216 (1992); and Wen et al., *Cell*, 69:559-572 (1992). Like the HRG polypeptides, NDF has an immunoglobulin (Ig) homology domain followed by an EGF-like domain and lacks a N-terminal signal peptide. Subsequently, Wen et al., *Mol. Cell. Biol.*, 14(3):1909-1919 (1994) carried out "exhaustive cloning" to extend the family of NDFs. This work revealed six distinct fibroblastic pro-NDFs. Adopting the nomenclature of Holmes et al., the NDFs are classified as either α or β, polypeptides based on the sequences of the EGF-like domains. Isoforms 1 to 4 are characterized on the basis of the variable juxtamembrane stretch (between the EGF-like domain and transmembrane domain). Also, isoforms a, b and c are described which have variable length cytoplasmic domains. These researchers conclude that different NDF isoforms are generated by alternative splicing and perform distinct tissue-specific functions.

Falls et al., *Cell*, 72:801-815 (1993) describe another member of the heregulin family which they call acetylcholine receptor inducing activity (ARIA) polypeptide. The chicken-derived ARIA polypeptide stimulates synthesis of muscle acetylcholine receptors. See also WO 94/08007. ARIA is a β-type heregulin and lacks the entire "glyco" spacer (rich in glycosylation sites) present between the Ig-like domain and EGF-like domain of HRGα, and HRGβ1-β3.

Marchionni et al., *Nature*, 362:312-318 (1993) identified several bovine-derived proteins which they call glial growth factors (GGFs). These GGFs share the Ig-like domain and EGF-like domain with the other heregulin proteins described above, but also have an amino-terminal kringle domain. GGFs generally do not have the complete "glyco" spacer between the Ig-like domain and EGF-like domain. Only one of the GGFs, GGFII, possessed a N-terminal signal peptide.

Expression of the ErbB2 family of receptors and heregulin polypeptides in breast cancer is reviewed in Bacus et al., *Pathology Patterns*, 102(4)(Supp. 1):S13-S24 (1994).

See also, Alimandi et al., *Oncogene*, 10: 1813-1821 (1995); Beerli et al., *Molecular and Cellular Biology*, 15:6496-6505 (1995); Karunagaran et al., *EMBO J*, 15:254-264 (1996); Wallasch et al., *EMBO J*, 14:4267-4275 (1996); and Zhang et al., *Journal of Biological Chemistry*, 271: 3884-3890 (1996), in relation to the above receptor family.

SUMMARY OF THE INVENTION

This invention provides antibodies which bind to ErbB3 protein and further possess any one or more of the following properties: an ability to reduce heregulin-induced formation of an ErbB2-ErbB3 protein complex in a cell which expresses ErbB2 and ErbB3; the ability to increase the binding affinity of heregulin for ErbB3 protein; and the characteristic of reducing heregulin-induced ErbB2 activation in a cell which expresses ErbB2 and ErbB3.

The invention also relates to an antibody which binds to ErbB3 protein and reduces heregulin binding thereto.

Preferred antibodies are monoclonal antibodies which bind to an epitope in the extracellular domain of the ErbB3 receptor. Generally, antibodies of interest will bind the ErbB3 receptor with an affinity of at least about 10 nM, more preferably at least about 1 nM. In certain embodiments, the antibody is immobilized on (e.g. covalently attached to) a solid phase, e.g., for affinity purification of the receptor or for diagnostic assays.

The antibodies of the preceding paragraphs may be provided in the form of a composition comprising the antibody and a pharmaceutically acceptable carrier or diluent.

The invention also provides: an isolated nucleic acid molecule encoding the antibody of the preceding paragraphs which may further comprise a promoter operably linked thereto; an expression vector comprising the nucleic acid molecule operably linked to control sequences recognized by a host cell transformed with the vector; a cell line comprising the nucleic acid (e.g. a hybridoma cell line); and a process of using a nucleic acid molecule encoding the antibody to effect production of the antibody comprising culturing a cell comprising the nucleic acid and, optionally, recovering the antibody from the cell culture and, preferably, the cell culture medium.

The invention also provides a method for treating a mammal comprising administering a therapeutically effective amount of the antibody described herein to the mammal, wherein the mammal has a disorder requiring treatment with the antibody.

In a further aspect, the invention provides a method for detecting ErbB3 in vitro or in vivo comprising contacting the antibody with a cell suspected of containing ErbB3 and detecting if binding has occurred. Accordingly, the invention provides an assay for detecting a tumor characterized by amplified expression of ErbB3 comprising the steps of exposing a cell to the antibody disclosed herein and determining the extent of binding of the antibody to the cell. Generally the antibody for use in such an assay will be labelled. The assay herein may be an in vitro assay (such as an ELISA assay) or an in vivo assay. For in vivo tumor diagnosis, the antibody is generally conjugated to a radioactive isotope and administered to a mammal, and the extent of binding of the antibody to tissues in the mammal is observed by external scanning for radioactivity.

BRIEF DESCRIPTION OF THE DRAWINGS

FIG. 1 depicts HRG binding to K562 ErbB3 cells in the presence of various anti-ErbB3 monoclonal antibodies. Purified anti-ErbB3 antibodies were incubated with a suspension of K562 ErbB3 cells and $^{125}$I-HRGβ1$_{(177-244)}$. After approximately 18 hours on ice, cell bound counts were measured. Counts are shown plotted as a percentage of binding in the absence of antibody (control). Non-specific binding was determined using an excess of unlabeled HRGβ1$_{(177-244)}$(HRG). Antibodies against ErbB2 protein (2C4) and HSV (5B6) were used as negative controls.

FIG. 2 shows the effect of antibody concentration on HRG binding. A dose-response experiment was performed on the 3-8D6 antibody which was found to enhance HRG binding. K562 ErbB3 cells were incubated with a fixed concentration of $^{125}$I-HRG and increasing concentrations of the 3-8D6 antibody. Data from the experiment is shown plotted as cell bound counts versus antibody concentration FIG. 3 illustrates HRG binding to K562 ErbB3 cells in the presence and absence of the 3-8D6 antibody or a Fab fragment thereof. Competitive ligand binding experiments were performed in the absence (control) and presence of 100 nM 3-8D6 or Fab. The data are plotted as bound/total (B/T) versus total HRGβ1$_{(177-244)}$.

DETAILED DESCRIPTION OF THE PREFERRED EMBODIMENTS

I. Definitions

Unless indicated otherwise, the term "ErbB3" when used herein refers to mammalian ErbB3 protein and "erbB3" refers to mammalian erbB3 gene. The preferred ErbB3 protein is human ErbB3 protein present in the cell membrane of a cell. The human erbB3 gene is described in U.S. Pat. No. 5,480,968 and Plowman et al., *Proc. Natl. Acad. Sci. USA,* 87:4905-4909 (1990).

The antibody of interest may be one which does not significantly cross-react with other proteins such as those encoded by the erbB1, erbB2 and/or erbB4 genes. In such embodiments, the extent of binding of the antibody to these non-ErbB3 proteins (e.g., cell surface binding to endogenous receptor) will be less than 10% as determined by fluorescence activated cell sorting (FACS) analysis or radioimmunoprecipitation (RIA). However, sometimes the antibody may be one which does cross-react with ErbB4 receptor, and, optionally, does not cross-react with the EGFR and/or ErbB2 receptor, for example.

"Heregulin" (HRG) when used herein refers to a polypeptide which activates the ErbB2-ErbB3 protein complex (i.e. induces phosphorylation of tyrosine residues in the ErbB2-ErbB3 complex upon binding thereto). Various heregulin polypeptides encompassed by this term have been disclosed above. The term includes biologically active fragments and/or variants of a naturally occurring HRG polypeptide, such as an EGF-like domain fragment thereof (e.g. HRGβ1$_{177-244}$).

The "ErbB2-ErbB3 protein complex" is a noncovalently associated oligomer of the ErbB2 receptor and the ErbB3 receptor. This complex forms when a cell expressing both of these receptors is exposed to HRG. The complex can be isolated by immunoprecipitation and analyzed by SDS-PAGE as described in the Example below.

The expression "reduces heregulin-induced formation of an ErbB2-ErbB3 protein complex in a cell which expresses ErbB2 and ErbB3" refers to the ability of the antibody to statistically significantly reduce the number of ErbB2-ErbB3 protein complexes which form in a cell which has been exposed to the antibody and HRG relative to an untreated (control) cell. The cell which expresses ErbB2 and ErbB3 can be a naturally occurring cell or cell line (e.g. Caov3 cell) or can be recombinantly produced by introducing nucleic acid encoding each of these proteins into a host cell. Preferably, the antibody will reduce formation of this complex by at least 50%, and more preferably at least 70%, as determined by reflectance scanning densitometry of Western blots of the complex (see the Example below).

The antibody which "reduces heregulin-induced ErbB2 activation in a cell which expresses ErbB2 and ErbB3" is one which statistically significantly reduces tyrosine phosphorylation activity of ErbB2 which occurs when HRG binds to ErbB3 in the ErbB2-ErbB3 protein complex (present at the surface of a cell which expresses the two receptors) relative to an untreated (control) cell. This can be determined based on phosphotyrosine levels in the ErbB2-ErbB3 complex following exposure of the complex to HRG and the antibody of interest. The cell which expresses ErbB2 and ErbB3 protein can be a naturally occurring cell or cell line (e.g. Caov3 cell) or can be recombinantly produced. ErbB2 activation can be determined by Western blotting followed by probing with an anti-phosphotyrosine antibody as described in the Example below. Alternatively, the kinase receptor activation assay described in WO 95/14930 and Sadick et al., *Analytical Biochemistry,* 235:207-214 (1996) can be used to quantify ErbB2 activation. Preferably, the antibody will reduce heregulin-induced ErbB2 activation by at least 50%, and more preferably at least 70%, as determined by reflectance scanning densitometry of Western blots of the complex probed with an anti-phosphotyrosine antibody (see the Example below).

The antibody may be one which "increases the binding affinity of heregulin for ErbB3 protein". This means that, in the presence of the antibody (e.g. 100 nM antibody), the amount of HRG which binds to ErbB3 (e.g., endogenous ErbB3 present in a naturally occurring cell or cell line or introduced into a cell by recombinant techniques, see the Example below), relative to control (no antibody), is statistically significantly increased. For example, the amount of HRG which binds to the K562 cell line transfected with erbB3 as described herein may be increased in the presence of 100 nM antibody by at least 10% preferably at least 50% and most preferably at least about 100% (see FIG. 1), relative to control.

The antibody which reduces HRG binding to ErbB3 protein (e.g. ErbB3 present in a cell) is one which interferes with the HRG-binding site on ErbB3 protein such that it statistically significantly decreases the amount of heregulin which is able to bind to this site on the molecule. Exemplary such antibodies are the 3-2F9, 3-3E9 and 3-6B9 antibodies described in the Example herein.

The term "antibody" is used in the broadest sense and specifically covers intact monoclonal antibodies, polyclonal antibodies, multispecific antibodies (e.g. bispecific antibodies) formed from at least two intact antibodies, and antibody fragments so long as they exhibit the desired biological activity. The antibody may be an IgM, IgG (e.g. IgG$_1$, IgG$_2$, IgG$_3$ or IgG$_4$), IgD, IgA or IgE, for example. Preferably however, the antibody is not an IgM antibody.

"Antibody fragments" comprise a portion of an intact antibody, generally the antigen binding or variable region of the intact antibody. Examples of antibody fragments include Fab, Fab', F(ab')$_2$, and Fv fragments; diabodies; single-chain antibody molecules; and multispecific antibodies formed from antibody fragments.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations which typically include different antibodies directed against different determinants (epitopes), each monoclonal antibody is directed against a single determinant on the antigen. In addition to their specificity, the monoclonal antibodies are advantageous in that they are synthesized by the hybridoma culture, uncontaminated by other immunoglobulins. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al., *Nature,*

256:495 (1975), or may be made by recombinant DNA methods (see, e.g., U.S. Pat. No. 4,816,567). The "monoclonal antibodies" may also be isolated from phage antibody libraries using the techniques described in Clackson et al., *Nature,* 352:624-628 (1991) and Marks et al., *J. Mol. Biol.,* 222:581-597 (1991), for example.

The monoclonal antibodies herein specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; Morrison et al., *Proc. Natl. Acad. Sci. USA,* 81:6851-6855 (1984)).

"Humanized" forms of non-human (e.g., murine) antibodies are chimeric immunoglobulins, immunoglobulin chains or fragments thereof (such as Fv, Fab, Fab', F(ab')$_2$ or other antigen-binding subsequences of antibodies) which contain minimal sequence derived from non-human immunoglobulin. For the most part, humanized antibodies are human immunoglobulins (recipient antibody) in which residues from a complementarity-determining region (CDR) of the recipient are replaced by residues from a CDR of a non-human species (donor antibody) such as mouse, rat or rabbit having the desired specificity, affinity, and capacity. In some instances, Fv framework region (FR) residues of the human immunoglobulin are replaced by corresponding non-human residues. Furthermore, humanized antibodies may comprise residues which are found neither in the recipient antibody nor in the imported CDR or framework sequences. These modifications are made to further refine and optimize antibody performance. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin sequence. The humanized antibody optimally also will comprise at least a portion of an immunoglobulin constant region (Fc), typically that of a human immunoglobulin. For further details, see Jones et al., *Nature,* 321:522-525 (1986); Reichmann et al., *Nature,* 332:323-329 (1988); and Presta, *Curr. Op. Struct. Biol.,* 2:593-596 (1992). The humanized antibody includes a Primatized™antibody wherein the antigen-binding region of the antibody is derived from an antibody produced by immunizing macaque monkeys with the antigen of interest.

"Single-chain Fv" or "sFv" antibody fragments comprise the $V_H$ and $V_L$ domains of antibody, wherein these domains are present in a single polypeptide chain. Generally, the Fv polypeptide further comprises a polypeptide linker between the $V_H$ and $V_L$ domains which enables the sFv to form the desired structure for antigen binding. For a review of sFv see Pluckthun in *The Pharmacology of Monoclonal Antibodies,* vol. 113, Rosenburg and Moore eds., Springer-Verlag, New York, pp. 269-315 (1994).

The term "diabodies" refers to small antibody fragments with two antigen-binding sites, which fragments comprise a heavy-chain variable domain ($V_H$) connected to a light-chain variable domain ($V_L$) in the same polypeptide chain ($V_H$-$V_L$). By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Hollinger et al., *Proc. Natl. Acad. Sci. USA,* 90:6444-6448 (1993).

An "isolated" antibody is one which has been identified and separated and/or recovered from a component of its natural environment. Contaminant components of its natural environment are materials which would interfere with diagnostic or therapeutic uses for the antibody, and may include enzymes, hormones, and other proteinaceous or nonproteinaceous solutes. In preferred embodiments, the antibody will be purified (1) to greater than 95% by weight of antibody as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step.

As used herein, the term "salvage receptor binding epitope" refers to an epitope of the Fc region of an IgG molecule (e.g., $IgG_1$, $IgG_2$, $IgG_3$, or $IgG_4$) that is responsible for increasing the in vivo serum half-life of the IgG molecule.

"Treatment" refers to both therapeutic treatment and prophylactic or preventative measures. Those in need of treatment include those already with the disorder as well as those in which the disorder is to be prevented.

"Mammal" for purposes of treatment refers to any animal classified as a mammal, including humans, domestic and farm animals, and zoo, sports, or pet animals, such as dogs, horses, cats, cows, etc. Preferably, the mammal is human.

A "disorder" is any condition that would benefit from treatment with the anti-ErbB3 antibody. This includes chronic and acute disorders or diseases including those pathological conditions which predispose the mammal to the disorder in question. Generally, the disorder will be one in which excessive activation of the ErbB2-ErbB3 protein complex by heregulin is occurring. Non-limiting examples of disorders to be treated herein include benign and malignant tumors; leukemias and lymphoid malignancies; neuronal, glial, astrocytal, hypothalamic and other glandular, macrophagal, epithelial, stromal and blastocoelic disorders; and inflammatory, angiogenic and immunologic disorders.

The terms "cancer" and "cancerous" refer to or describe the physiological condition in mammals that is typically characterized by unregulated cell growth. Examples of cancer include but are not limited to, carcinoma, lymphoma, blastoma, sarcoma, and leukemia. More particular examples of such cancers include squamous cell cancer, small-cell lung cancer, non-small cell lung cancer, gastrointestinal cancer, pancreatic cancer, glioblastoma, cervical cancer, ovarian cancer, liver cancer, bladder cancer, hepatoma, breast cancer, colon cancer, colorectal cancer, endometrial carcinoma, salivary gland carcinoma, kidney cancer, renal cancer, prostate cancer, vulval cancer, thyroid cancer, hepatic carcinoma and various types of head and neck cancer.

The term "cytotoxic agent" as used herein refers to a substance that inhibits or prevents the function of cells and/or causes destruction of cells. The term is intended to include radioactive isotopes (e.g. I, Y, Pr), chemotherapeutic agents, and toxins such as enzymatically active toxins of bacterial fungal plant or animal origin, or fragments thereof.

A "chemotherapeutic agent" is a chemical compound useful in the treatment of cancer. Examples of chemotherapeutic agents include Adriamycin, Doxorubicin, 5-Fluorouracil, Cytosine arabinoside ("Ara-C"), Cyclophosphamide, Thiotepa, Busulfan, Cytoxin, Taxol, Methotrexate, Cisplatin, Melphalan, Vinblastine, Bleomycin, Etoposide, Ifosfamide, Mitomycin C, Mitoxantrone, Vincreistine, Vinorelbine, Carboplatin, Teniposide, Daunomycin, Carminomycin, Aminopterin, Dactinomycin, Mitomycins, Esperamicins (see U.S. Pat. No. 4,675,187), Melphalan and other related nitrogen mustards.

The term "cytokine" is a generic term for proteins released by one cell population which act on another cell as intercellular mediators. Examples of such cytokines are lymphokines, monokines, and traditional polypeptide hormones. Included among the cytokines are growth hormone such as human growth hormone, N-methionyl human growth hormone, and bovine growth hormone; parathyroid hormone; thyroxine; insulin proinsulin; relaxin; prorelaxin; glycoprotein hormones such as follicle stimulating hormone (FSH), thyroid stimulating hormone (TSH), and luteinizing hormone (LH); hepatic growth factor; fibroblast growth factor; prolactin; placental lactogen; tumor necrosis factor-α and -β; mullerian-inhibiting substance; mouse gonadotropin-associated peptide; inhibin; activin; vascular endothelial growth factor; integrin; thrombopoietin (TPO); nerve growth factors such as NGF-β; platelet-growth factor; transforming growth factors (TGFs) such as TGF-α and TGF-β; insulin-like growth factor-I and -II; erythropoietin (EPO); osteoinductive factors; interferons such as interferon-α, -β, and -γ; colony stimulating factors (CSFs) such as macrophage-CSF (M-CSF); granulocyte-macrophage-CSF (GM-CSF); and granulocyte-CSF (G-CSF); interleukins (ILs) such as IL-1, IL-1α, IL-2, IL3, IL4, IL5, IL6, IL7, IL-8, IL-11, IL-12; a tumor necrosis factor such as TNF-α or TNF-β; and other polypeptide factors including LIF and kit ligand (KL). As used herein, the term cytokine includes proteins from natural sources or from recombinant cell culture and biologically active equivalents of the native sequence cytokines.

The term "prodrug" as used in this application refers to a precursor or derivative form of a pharmaceutically active substance that is less cytotoxic to tumor cells compared to the parent drug and is capable of being enzymatically activated or converted into the more active parent form. See, e.g., Wilman, "Prodrugs in Cancer Chemotherapy" *Biochemical Society Transactions*, 14, pp. 375-382, 615th Meeting Belfast (1986) and Stella et al., "Prodrugs: A Chemical Approach to Targeted Drug Delivery," *Directed Drug Delivery*, Borchardt et al., (ed.), pp. 247-267, Humana Press (1985). The prodrugs of this invention include, but are not limited to, phosphate-containing prodrugs, thiophosphate-containing prodrugs, sulfate-containing prodrugs, peptide-containing prodrugs, D-amino acid-modified prodrugs, glycosylated prodrugs, β-lactam-containing prodrugs, optionally substituted phenoxyacetamide-containing prodrugs or optionally substituted phenylacetamide-containing prodrugs, 5-fluorocytosine and other 5-fluorouridine prodrugs which can be converted into the more active cytotoxic free drug. Examples of cytotoxic drugs that can be derivatized into a prodrug form for use in this invention include, but are not limited to, those chemotherapeutic agents described above.

The word "label" when used herein refers to a detectable compound or composition which is conjugated directly or indirectly to the antibody. The label may be detectable by itself (e.g. radioisotope labels or fluorescent labels) or, in the case of an enzymatic label, may catalyze chemical alteration of a substrate compound or composition which is detectable.

By "solid phase" is meant a non-aqueous matrix to which the antibody of the present invention can adhere. Examples of solid phases encompassed herein include those formed partially or entirely of glass (e.g.,controlled pore glass), polysaccharides (e.g., agarose), polyacrylamides, polystyrene, polyvinyl alcohol and silicones. In certain embodiments, depending on the context, the solid phase can comprise the well of an assay plate; in others it is a purification column (e.g.,an affinity chromatography column). This term also includes a discontinuous solid phase of discrete particles, such as those described in U.S. Pat. No. 4,275,149.

A "liposome" is a small vesicle composed of various types of lipids, phospholipids and/or surfactant which is useful for delivery of a drug (such as the anti-ErbB3 antibodies disclosed herein and, optionally, a chemotherapeutic agent) to a mammal. The components of the liposome are commonly arranged in a bilayer formation, similar to the lipid arrangement of biological membranes.

An "isolated" nucleic acid molecule is a nucleic acid molecule that is identified and separated from at least one contaminant nucleic acid molecule with which it is ordinarily associated in the natural source of the antibody nucleic acid. An isolated nucleic acid molecule is other than in the form or setting in which it is found in nature. Isolated nucleic acid molecules therefore are distinguished from the nucleic acid molecule as it exists in natural cells. However, an isolated nucleic acid molecule includes a nucleic acid molecule contained in cells that ordinarily express the antibody where, for example, the nucleic acid molecule is in a chromosomal location different from that of natural cells.

The expression "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

As used herein, the expressions "cell," "cell line," and "cell culture" are used interchangeably and all such designations include progeny. Thus, the words "transformants" and "transformed cells" include the primary subject cell and cultures derived therefrom without regard for the number of transfers. It is also understood that all progeny may not be precisely identical in DNA content, due to deliberate or inadvertent mutations. Mutant progeny that have the same function or biological activity as screened for in the originally transformed cell are included. Where distinct designations are intended, it will be clear from the context.

II. Modes for Carrying out the Invention

A. Antibody Preparation

A description follows as to exemplary techniques for the production of the claimed antibodies.

(i) Polyclonal Antibodies

Polyclonal antibodies are generally raised in animals by multiple subcutaneous (sc) or intraperitoneal (ip) injections of the relevant antigen and an adjuvant. It may be useful to conjugate the relevant antigen to a protein that is immunogenic in the species to be immunized, e.g., keyhole limpet hemocyanin, serum albumin, bovine thyroglobulin, or soybean trypsin inhibitor using a bifunctional or derivatizing agent, for example, maleimidobenzoyl sulfosuccinimide ester (conjugation through cysteine residues), N-hydroxysuccinimide (through lysine residues), glutaraldehyde, succinic anhydride, $SOCl_2$, or $R^1N=C=NR$, where R and $R^1$ are different alkyl groups.

Animals are immunized against the antigen, immunogenic conjugates, or derivatives by combining, e.g., 100 µg or 5 µg of the protein or conjugate (for rabbits or mice., respectively) with 3 volumes of Freund's complete adjuvant and injecting the solution intradermally at multiple sites. One month later the animals are boosted with ⅕ to ¹⁄₁₀ the original amount of peptide or conjugate in Freund's complete adjuvant by subcutaneous injection at multiple sites. Seven to 14 days later the animals are bled and the serum is assayed for antibody titer. Animals are boosted until the titer plateaus. Preferably, the animal is boosted with the conjugate of the same antigen, but conjugated to a different protein and/or through a different cross-linking reagent. Conjugates also can be made in recombinant cell culture as protein fusions. Also, aggregating agents such as alum are suitably used to enhance the immune response.

(ii) Monoclonal Antibodies

Monoclonal antibodies are obtained from a population of substantially homogeneous antibodies, i.e., the individual antibodies comprising the population are identical except for possible naturally occurring mutations that may be present in minor amounts. Thus, the modifier "monoclonal" indicates the character of the antibody as not being a mixture of discrete antibodies.

For example, the monoclonal antibodies may be made using the hybridoma method first described by Kohler et al., *Nature*, 256:495 (1975), or may be made by recombinant DNA methods (U.S. Pat. No. 4,816,567).

In the hybridoma method, a mouse or other appropriate host animal, such as a hamster, is immunized as hereinabove described to elicit lymphocytes that produce or are capable of producing antibodies that will specifically bind to the protein used for immunization Alternatively, lymphocytes may be immunized in vitro. Lymphocytes then are fused with myeloma cells using a suitable fusing agent, such as polyethylene glycol, to form a hybridoma cell (Goding, *Monoclonal Antibodies: Principles and Practice*, pp.59-103 (Academic Press, 1986)).

The hybridoma cells thus prepared are seeded and grown in a suitable culture medium that preferably contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

Preferred myeloma cells are those that fuse efficiently, support stable high-level production of antibody by the selected antibody-producing cells, and are sensitive to a medium such as HAT medium. Among these, preferred myeloma cell lines are murine myeloma lines, such as those derived from MOPC-21 and MPG-11 mouse tumors available from the Salk Institute Cell Distribution Center, San Diego, Calif. USA, and SP-2 or X63-Ag8-653 cells available from the American Type Culture Collection, Rockville, Md. USA. Human myeloma and mouse-human heteromyeloma cell lines also have been described for the production of human monoclonal antibodies (Kozbor, *J. Immunol.*, 133:3001 (1984); Brodeur et al., *Monoclonal Antibody Production Techniques and Applications*, pp. 51-63 (Marcel Dekker, Inc., New York, 1987)).

Culture medium in which hybridoma cells are growing is assayed for production of monoclonal antibodies directed against the antigen. Preferably, the binding specificity of monoclonal antibodies produced by hybridoma cells is determined by immunoprecipitation or by an in vitro binding assay, such as radioimmunoassay (RIA) or enzyme-linked immunoabsorbent assay (ELISA).

The binding affinity of the monoclonal antibody can, for example, be determined by the Scatchard analysis of Munson et al., *Anal. Biochem.*, 107:220 (1980).

After hybridoma cells are identified that produce antibodies of the desired specificity, affinity, and/or activity, the clones may be subcloned by limiting dilution procedures and grown by standard methods (Goding, *Monoclonal Antibodies: Principles and Practice*, pp. 59-103 (Academic Press, 1986)). Suitable culture media for this purpose include, for example, D-MEM or RPMI-1640 medium. In addition, the hybridoma cells may be grown in vivo as ascites tumors in an animal.

The monoclonal antibodies secreted by the subclones are suitably separated from the culture medium, ascites fluid, or serum by conventional immunoglobulin purification procedures such as, for example, protein A-Sepharose, hydroxylapatite chromatography, gel electrophoresis, dialysis, or affinity chromatography.

DNA encoding the monoclonal antibodies is readily isolated and sequenced using conventional procedures (e.g., by using oligonucleotide probes that are capable of binding specifically to genes encoding the heavy and light chains of murine antibodies). The hybridoma cells serve as a preferred source of such DNA Once isolated, the DNA may be placed into expression vectors, which are then transfected into host cells such as *E. coli* cells, simian COS cells, Chinese hamster ovary (CHO) cells, or myeloma cells that do not otherwise produce immunoglobulin protein, to obtain the synthesis of monoclonal antibodies in the recombinant host cells. Review articles on recombinant expression in bacteria of DNA encoding the antibody include Skerra et al., *Curr. Opinion in Immunol.*, 5:256-262 (1993) and Plückthun, *Immunol. Revs.*, 130:151-188 (1992).

In a further embodiment, antibodies or antibody fragments can be isolated from antibody phage libraries generated using the techniques described in McCafferty et al., *Nature*, 348:552-554 (1990). Clackson et al., *Nature*, 352: 624-628 (1991) and Marks et al., *J. Mol. Biol.*, 222:581-597 (1991) describe the isolation of murine and human antibodies, respectively, using phage libraries. Subsequent publications describe the production of high affinity (nM range) human antibodies by chain shuffling (Marks et al., *Bio/Technology*, 10:779-783 (1992)), as well as combinatorial infection and in vivo recombination as a strategy for constructing very large phage libraries (Waterhouse et al., *Nuc. Acids. Res.*, 21:2265-2266 (1993)). Thus, these techniques are viable alternatives to traditional monoclonal antibody hybridoma techniques for isolation of monoclonal antibodies.

The DNA also may be modified, for example, by substituting the coding sequence for human heavy- and light-chain constant domains in place of the homologous murine sequences (U.S. Pat. No. 4,816,567; Morrison, et al., *Proc. Natl Acad. Sci. USA,* 81:6851 (1984)), or by covalently joining to the immunoglobulin coding sequence all or part of the coding sequence for a non-immunoglobulin polypeptide.

Typically such non-immunoglobulin polypeptides are substituted for the constant domains of an antibody, or they are substituted for the variable domains of one antigen-combining site, of an antibody to create a chimeric bivalent antibody comprising one antigen-combining site having specificity for an antigen and another antigen-combining site having specificity for a different antigen.

(iii) Humanized and Human Antibodies

Methods for humanizing non-human antibodies are well known in the art. Generally, a humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers (Jones et al., *Nature,* 321:522-525 (1986); Riechmann et al., *Nature,* 332:323-327 (1988); Verhoeyen et al., *Science,* 239:1534-1536 (1988)), by substituting rodent CDRs or CDR sequences for the corresponding sequences of a human antibody. Accordingly, such "humanized" antibodies are chimeric antibodies (U.S. Pat. No. 4,816,567) wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

The choice of human variable domains, both light and heavy, to be used in making the humanized antibodies is very important to reduce antigenicity. According to the so-called "best-fit" method, the sequence of the variable domain of a rodent antibody is screened against the entire library of known human variable-domain sequences. The human sequence which is closest to that of the rodent is then accepted as the human framework (FR) for the humanized antibody (Sims et al., *J. Immunol.,* 151:2296 (1993); Chothia et al., *J. Mol. Biol.,* 196:901 (1987)). Another method uses a particular framework derived from the consensus sequence of all human antibodies of a particular subgroup of light or heavy chains. The same framework may be used for several different humanized antibodies (Carter et al., *Proc. Natl. Acad. Sci. USA,* 89:4285 (1992); Presta et al., *J. Immnol.,* 151:2623 (1993)).

It is further important that antibodies be humanized with retention of high affinity for the antigen and other favorable biological properties. To achieve this goal, according to a preferred method, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired antibody characteristic, such as increased affinity for the target antigen(s), is achieved. In general, the CDR residues are directly and most substantially involved in influencing antigen binding.

Alternatively, it is now possible to produce transgenic animals (e.g., mice) that are capable, upon immunization, of producing a full repertoire of human antibodies in the absence of endogenous immunoglobulin production. For example, it has been described that the homozygous deletion of the antibody heavy-chain joining region ($J_H$) gene in chimeric and germ-line mutant mice results in complete inhibition of endogenous antibody production. Transfer of the human germ-line immunoglobulin gene array in such germ-line mutant mice will result in the production of human antibodies upon antigen challenge. See, e.g., Jakobovits et al., *Proc. Natl. Acad. Sci. USA,* 90:2551 (1993); Jakobovits et al., *Nature,* 362:255-258 (1993); Bruggermann et al., *Year in Immuno.,* 7:33 (1993). Human antibodies can also be derived from phage-display libraries (Hoogenboom et al., *J. Mol. Biol.,* 227:381 (1991); Marks et al., *J. Mol. Biol.,* 222:581-597 (1991)).

(iv) Antibody Fragments

Various techniques have been developed for the production of antibody fragments. Traditionally, these fragments were derived via proteolytic digestion of intact antibodies (see, e.g., Morimoto et al., *Journal of Biochemical and Biophysical Methods* 24:107-117 (1992) and Brennan et al., *Science,* 229:81 (1985)). However, these fragments can now be produced directly by recombinant host cells. For example, the antibody fragments can be isolated from the antibody phage libraries discussed above. Alternatively, Fab'-SH fragments can be directly recovered from *E. coli* and chemically coupled to form F(ab')$_2$ fragments (Carter et al., *Bio/Technology* 10: 163-167 (1992)). According to another approach, F(ab')$_2$ fragments can be isolated directly from recombinant host cell culture. Other techniques for the production of antibody fragments will be apparent to the skilled practitioner.

(v) Bispecific Antibodies

Bispecific antibodies are antibodies that have binding specificities for at least two different epitopes. Exemplary bispecific antibodies may bind to two different epitopes of the ErbB3 protein. Other such antibodies may combine an ErbB3 binding site with binding site(s) for EGFR, ErbB2 and/or ErbB4. Alternatively, an anti-ErbB3 arm may be combined with an arm which binds to a triggering molecule on a leukocyte such as a T-cell receptor molecule (e.g. CD2 or CD3), or Fc receptors for IgG (Fcγ R), such as Fcγ RI (CD64), Fcγ RII (CD32) and Fcγ RIII (CD16) so as to focus cellular defense mechanisms to the ErbB3-expressing cell. Bispecific antibodies may also be used to localize cytotoxic agents to cells which express ErbB3. These antibodies possess an ErbB3-binding arm and an arm which binds the cytotoxic agent (e.g. saporin, anti-interferon-α, vinca alkaloid, ricin A chain, methotrexate or radioactive isotope hapten). Bispecific antibodies can be prepared as full length antibodies or antibody fragments (e.g. F(ab')$_2$ bispecific antibodies).

Methods for making bispecific antibodies are known in the art. Traditional production of full length bispecific antibodies is based on the coexpression of two immunoglobulin heavy chain-light chain pairs, where the two chains have different specificities (Millstein et al., *Nature,* 305:537-539

(1983)). Because of the random assortment of immunoglobulin heavy and light chains, these hybridomas (quadromas) produce a potential mixture of 10 different antibody molecules, of which only one has the correct bispecific structure. Purification of the correct molecule, which is usually done by affinity chromatography steps, is rather cumbersome, and the product yields are low. Similar procedures are disclosed in WO 93/08829, and in Traunecker et al., *EMBO J.*, 10:3655-3659 (1991).

According to a different approach, antibody variable domains with the desired binding specificities (antibody-antigen combining sites) are fused to immunoglobulin constant domain sequences. The fusion preferably is with an immunoglobulin heavy chain constant domain, comprising at least part of the hinge, CH2, and CH3 regions. It is preferred to have the first heavy-chain constant region (CH1) containing the site necessary for light chain binding, present in at least one of the fusions. DNAs encoding the immunoglobulin heavy chain fusions and, if desired, the immunoglobulin light chain, are inserted into separate expression vectors, and are co-transfected into a suitable host organism. This provides for great flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains in one expression vector when the expression of at least two polypeptide chains in equal ratios results in high yields or when the ratios are of no particular significance.

In a preferred embodiment of this approach, the bispecific antibodies are composed of a hybrid immunoglobulin heavy chain with a first binding specificity in one arm, and a hybrid immunoglobulin heavy chain-light chain pair (providing a second binding specificity) in the other arm. It was found that this asymmetric structure facilitates the separation of the desired bispecific compound from unwanted immunoglobulin chain combinations, as the presence of an immunoglobulin light chain in only one half of the bispecific molecule provides for a facile way of separation. This approach is disclosed in WO 94/04690. For further details of generating bispecific antibodies see, for example, Suresh et al., *Methods in Enzymology*, 121:210 (1986).

According to another approach, the interface between a pair of antibody molecules can be engineered to maximize the percentage of heterodimers which are recovered from recombinant cell culture. The preferred interface comprises at least a part of the $C_H3$ domain of an antibody constant domain. In this method, one or more small amino acid side chains from the interface of the first antibody molecule are replaced with larger side chains (e.g. tyrosine or tryptophan). Compensatory "cavities" of identical or similar size to the large side chain(s) are created on the interface of the second antibody molecule by replacing large amino acid side chains with smaller ones (e.g. alanine or threonine). This provides a mechanism for increasing the yield of the heterodimer over other unwanted end-products such as homodimers.

Bispecific antibodies include cross-linked or "heteroconjugate" antibodies. For example, one of the antibodies in the heteroconjugate can be coupled to avidin, the other to biotin. Such antibodies have, for example, been proposed to target immune system cells to unwanted cells (U.S. Pat. No. 4,676,980), and for treatment of HIV infection (WO 91/00360, WO 92/200373, and EP 03089). Heteroconjugate antibodies may be made using any convenient cross-linking methods. Suitable cross-linking agents are well known in the art, and are disclosed in U.S. Pat. No. 4,676,980, along with a number of cross-linking techniques.

Techniques for generating bispecific antibodies from antibody fragments have also been described in the literature. For example, bispecific antibodies can be prepared using chemical linkage. Brennan et al., *Science*, 229: 81 (1985) describe a procedure wherein intact antibodies are proteolytically cleaved to generate F(ab')$_2$ fragments. These fragments are reduced in the presence of the dithiol complexing agent sodium arsenite to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes.

Recent progress has facilitated the direct recovery of Fab'-SH fragments from *E. coli*, which can be chemically coupled to form bispecific antibodies. Shalaby et al., *J. Exp. Med.*, 175: 217-225 (1992) describe the production of a fully humanized bispecific antibody F(ab')$_2$ molecule. Each Fab' fragment was separately secreted from *E. coli* and subjected to directed chemical coupling in vitro to form the bispecific antibody. The bispecific antibody thus formed was able to bind to cells overexpressing the HER2 receptor and normal human T cells, as well as trigger the lytic activity of human cytotoxic lymphocytes against human breast tumor targets.

Various techniques for making and isolating bispecific antibody fragments directly from recombinant cell culture have also been described. For example, bispecific antibodies have been produced using leucine zippers. Kostelny et al., *J. Immunol.*, 148(5):1547-1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers. The "diabody" technology described by Hollinger et al., *Proc. Natl. Acad. Sci. USA*, 90:6444-6448 (1993) has provided an alternative mechanism for making bispecific antibody fragments. The fragments comprise a heavy-chain variable domain ($V_H$) connected to a light-chain variable domain ($V_L$) by a linker which is too short to allow pairing between the two domains on the same chain. Accordingly, the $V_H$ and $V_L$ domains of one fragment are forced to pair with the complementary $V_L$ and $V_H$ domains of another fragment, thereby forming two antigen-binding sites. Another strategy for making bispecific antibody fragments by the use of single-chain Fv (sFv) dimers has also been reported. See Gruber et al., *J. Immunol.*, 152:5368 (1994).

Antibodies with more than two valencies are contemplated. For example, trispecific antibodies can be prepared. Tutt et al. *J. Immunol.* 147: 60 (1991).

(vi) Screening for Antibodies with the Desired Properties

Techniques for generating antibodies have been described above. Those antibodies having the characteristics described herein are selected.

To select for antibodies which reduce HRG-induced formation of the ErbB2-ErbB3 protein complex, cells which express both these receptors (e.g. Caov3 cells) can be pre-incubated with buffer (control) or antibody, then treated with HRG or control buffer. The cells are then lysed and the crude lysates can be centrifuged to remove insoluble material. Supernatants may be incubated with an antibody specific for ErbB2 covalently coupled to a solid phase. Following washing, the immunoprecipitates may be separated by SDS-PAGE. Western blots of the gels are then probed with anti-ErbB3 antibody. After visualization, the blots may be stripped and re-probed with an anti-ErbB2 antibody. Reflectance scanning densitometry of the gel can be performed in order to quantify the effect of the antibody in question on HRG-induced formation of the complex. Those antibodies which reduce formation of the ErbB2-ErbB3 complex relative to control (untreated cells) can be selected. See the Example below.

To select for those antibodies which reduce HRG-induced ErbB2 activation in a cell which expresses the ErbB2 and ErbB3 receptor, the cells can be pre-incubated with buffer (control) or antibody, then treated with HRG or control buffer. The cells are then lysed and the crude lysates can be centrifuged to remove insoluble material. ErbB2 activation can be determined by Western blotting followed by probing with an anti-phosphotyrosine antibody as described in the Example below. ErbB2 activation can be quantified via reflectance, scanning densitometry of the gel, for example. Alternatively, the kinase receptor activation assay described in WO 95/14930 and Sadick et al., *Analytical Biochemistry*, 235:207-214 (1996) can be used to determine ErbB2 activation.

The effect of the antibody on HRG binding to ErbB3 can be determined by incubating cells which express this receptor (e.g. 4E9H3 cells transfected to express ErbB3) with radiolabelled HRG (e.g. the EGF-like domain thereof), in the absence (control) or presence of the anti-ErbB3 antibody, as described in the Example below, for example. Those antibodies which increase the binding affinity of HRG for the ErbB3 receptor can be selected for further development. Where the antibody of choice is one which blocks binding of HRG to ErbB3, those antibodies which do so in this assay can be identified.

To screen for antibodies which bind to the epitope on ErbB3 bound by an antibody of interest (e.g., those which block binding of the 3-8B8 antibody to ErbB3), a routine cross-blocking assay such as that described in *Antibodies, A Laboratory Manual*, Cold Spring Harbor Laboratory, Ed Harlow and David Lane (1988), can be performed.

(vii) Effector Function Engineering

It may be desirable to modify the antibody of the invention with respect to effector function, so as to enhance the effectiveness of the antibody in treating cancer, for example. For example cysteine residue(s) may be introduced in the Fc region, thereby allowing interchain disulfide bond formation in this region. The homodimeric antibody thus generated may have improved internalization capability and/or increased complement-mediated cell killing and antibody-dependent cellular cytotoxicity (ADCC). See Caron et al., *J. Exp Med.* 176:1191-1195 (1992) and Shopes, B. *J. Immunol.* 148:2918-2922 (1992). Homodimeric antibodies with enhanced anti-tumor activity may also be prepared using heterobifunctional cross-linkers as described in Wolff et al. *Cancer Research* 53:2560-2565 (1993). Alternatively, an antibody can be engineered which has dual Fc regions and may thereby have enhanced complement lysis and ADCC capabilities. See Stevenson et al. *Anti-Cancer Drug Design* 3:219-230 (1989).

(viii) Immunoconjugates

The invention also pertains to immunoconjugates comprising the antibody described herein conjugated to a cytotoxic agent such as a chemotherapeutic agent, toxin (e.g. an enzymatically active toxin of bacterial fungal, plant or animal origin, or fragments thereof), or a radioactive isotope (i.e., a radioconjugate).

Chemotherapeutic agents useful in the generation of such immunoconjugates have been described above. Enzymatically active toxins and fragments thereof which can be used include diphtheria A chain, nonbinding active fragments of diphtheria toxin, exotoxin A chain (from *Pseudomonas aeruginosa*); ricin A chain, abrin A chain, modeccin A chain, alpha-sarcin, *Aleurites fordii* proteins, dianthin proteins, *Phytolaca americana* proteins (PAPI, PAPII, and PAP-S), momordica charantia inhibitor, curcin, crotin, sapaonaria officinalis inhibitor, gelonin, mitogellin, restrictocin, phenomycin, enomycin and the tricothecenes. A variety of radionuclides are available for the production of radioconjugated anti-ErbB3 antibodies. Examples include $^{212}$Bi, $^{131}$I, $^{131}$In, $^{90}$Y and $^{186}$Re.

Conjugates of the antibody and cytotoxic agent are made using a variety of bifunctional protein coupling agents such as N-succinimidyl-3-(2-pyridyldithiol) propionate (SPDP), iminothiolane (IT), bifunctional derivatives of imidoesters (such as dimethyl adipimidate HCL), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene). For example, a ricin immunotoxin can be prepared as described in Vitetta et al. *Science* 238: 1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026.

In another embodiment, the antibody may be conjugated to a "receptor" (such streptavidin) for utilization in tumor pretargeting wherein the antibody-receptor conjugate is administered to the patient, followed by removal of unbound conjugate from the circulation using a clearing agent and then administration of a "ligand" (e.g. avidin) which is conjugated to a cytotoxic agent (e.g. a radionuclide).

(ix) Immunoliposomes

The anti-ErbB3 antibodies disclosed herein may also be formulated as immunoliposomes. Liposomes containing the antibody are prepared by methods known in the art, such as described in Epstein et al., *Proc. Natl. Acad. Sci. USA*, 82:3688 (1985); Hwang et al., *Proc. Natl Acad. Sci. USA*, 77:4030 (1980); and U.S. Pat. Nos. 4,485,045 and 4,544,545. Liposomes with enhanced circulation time are disclosed in U.S. Pat. No. 5,013,556.

Particularly useful liposomes can be generated by the reverse phase evaporation method with a lipid composition comprising phosphatidylcholine, cholesterol and PEG-derivatized phosphatidylethanolamine (PEG-PE). Liposomes are extruded-through filters of defined pore size to yield liposomes with the desired diameter. Fab' fragments of the antibody of the present invention can be conjugated to the liposomes as described in Martin et al. *J. Biol. Chem.* 257: 286-288 (1982) via a disulfide interchange reaction A chemotherapeutic agent (such as Doxorubicin) is optionally contained within the liposome. See Gabizon et al. *J. National Cancer Inst.*81(19)1484 (1989).

(x) Antibody Dependent Enzyme Mediated Prodrug Therapy (ADEPT)

The antibody of the present invention may also be used in ADEPT by conjugating the antibody to a prodrug-activating enzyme which converts a prodrug (e.g. a peptidyl chemotherapeutic agent, see WO81/01145) to an active anti-cancer drug. See, for example, WO 88/07378 and U.S. Pat. No. 4,975,278.

The enzyme component of the immunoconjugate useful for ADEPT includes any enzyme capable of acting on a prodrug in such a way so as to covert it into its more active, cytotoxic form.

Enzymes that are useful in the method of this invention include, but are not limited to, alkaline phosphatase useful for converting phosphate-containing prodrugs into free drugs; arylsulfatase useful for converting sulfate-containing prodrugs into free drugs; cytosine deaminase useful for converting non-toxic 5-fluorocytosine into the anti-cancer drug, 5-fluorouracil; proteases, such as serratia protease, thermolysin, subtilisin, carboxypeptidases and cathepsins (such as cathepsins B and L), that are useful for converting peptide-containing prodrugs into free drugs; D-alanylcarboxypeptidases, useful for converting prodrugs that contain D-amino acid substituents; carbohydrate-cleaving enzymes such as β-galactosidase and neuraminidase useful for converting glycosylated prodrugs into free drugs; β-lactamase useful for converting drugs derivatized with β-lactams into free drugs; and penicillin amidases, such as penicillin V amidase or penicillin G amidase, useful for converting drugs derivatized at their amine nitrogens with phenoxyacetyl or phenylacetyl groups, respectively, into free drugs. Alternatively, antibodies with enzymatic activity, also known in the art as "abzymes", can be used to convert the prodrugs of the invention into free active drugs (see, e.g., Massey, *Nature* 328: 457-458 (1987)). Antibody-abzyme conjugates can be prepared as described herein for delivery of the abzyme to a tumor cell population.

The enzymes of this invention can be covalently bound to the anti-ErbB3 antibodies by techniques well known in the art such as the use of the heterobifunctional crosslinking reagents discussed above. Alternatively, fusion proteins comprising at least the antigen binding region of an antibody of the invention linked to at least a functionally active portion of an enzyme of the invention can be constructed using recombinant DNA techniques well known in the art (see, e.g., Neuberger et al., *Nature,* 312: 604-608 (1984)).

(xi) Antibody-salvage Receptor Binding Epitope Fusions.

In certain embodiments of the invention, it may be desirable to use an antibody fragment, rather than an intact antibody, to increase tumor penetration, for example. In this case, it may be desirable to modify the antibody fragment in order to increase its serum half life. This may be achieved, for example, by incorporation of a salvage receptor binding epitope into the antibody fragment (e.g. by mutation of the appropriate region in the antibody fragment or by incorporating the epitope into a peptide tag that is then fused to the antibody fragment at either end or in the middle, e.g., by DNA or peptide synthesis).

A systematic method for preparing such an antibody variant having an increased in vivo half-life comprises several steps. The first involves identifying the sequence and conformation of a salvage receptor binding epitope of an Fc region of an IgG molecule. Once this epitope is identified, the sequence of the antibody of interest is modified to include the sequence and conformation of the identified binding epitope. After the sequence is mutated, the antibody variant is tested to see if it has a longer in vivo half-life than that of the original antibody. If the antibody variant does not have a longer in vivo half-life upon testing, its sequence is further altered to include the sequence and conformation of the identified binding epitope. The altered antibody is tested for longer in vivo half-life, and this process is continued until a molecule is obtained that exhibits a longer in vivo half-life.

The salvage receptor binding epitope being thus incorporated into the antibody of interest is any suitable such epitope as defined above, and its nature will depend, e.g., on the type of antibody being modified. The transfer is made such that the antibody of interest still possesses the biological activities described herein.

The epitope generally constitutes a region wherein any one or more amino acid residues from one or two loops of a Fc domain are transferred to an analogous position of the antibody fragment. Even more preferably, three or more residues from one or two loops of the Fc domain are transferred. Still more preferred, the epitope is taken from the CH2 domain of the Fc region (e.g., of an IgG) and transferred to the CH1, CH3, or $V_H$ region, or more than one such region, of the antibody. Alternatively, the epitope is taken from the CH2 domain of the Fc region and transferred to the $C_L$ region or $V_L$ region, or both, of the antibody fragment.

In one most preferred embodiment, the salvage receptor binding epitope comprises the sequence (5' to 3'): PKNSSMISNTP (SEQ ID NO: 1), and optionally further comprises a sequence selected from the group consisting of HQSLGTQ (SEQ ID NO: 2), HQNLSDGK (SEQ ID NO: 3), HQNISDGK (SEQ ID NO: 4), or VISSHLGQ (SEQ ID NO: 5), particularly where the antibody fragment is a Fab or F(ab')$_2$. In another most preferred embodiment, the salvage receptor binding epitope is a polypeptide containing the sequence(s)(5' to 3'): HQNLSDGK (SEQ ID NO: 3), HQNISDGK (SEQ ID NO: 4), or VISSHLGQ (SEQ ID NO: 5) and the sequence: PKNSSMISNTP (SEQ ID NO: 1).

B. Vectors, Host Cells and Recombinant Methods

The invention also provides isolated nucleic acid encoding an antibody as disclosed herein, vectors and host cells comprising the nucleic acid, and recombinant techniques for the production of the antibody.

For recombinant production of the antibody, the nucleic acid encoding it is isolated and inserted into a replicable vector for further cloning (amplification of the DNA) or for expression DNA encoding the monoclonal antibody is readily isolated and sequenced using conventional procedures (e.g., by using oligonucleotide probes that are capable of binding specifically to genes encoding the heavy and light chains of the antibody). Many vectors are available. The vector components generally include, but are not limited to, one or more of the following: a signal sequence, an origin of replication, one or more marker genes, an enhancer element, a promoter, and a transcription termination sequence.

(i) Signal Sequence Component

The anti-ErbB3 antibody of this invention may be produced recombinantly not only directly, but also as a fusion polypeptide with a heterologous polypeptide, which is preferably a signal sequence or other polypeptide having a specific cleavage site at the N-terminus of the mature protein or polypeptide. The heterologous signal sequence selected preferably is one that is recognized and processed (i.e., cleaved by a signal peptidase) by the host cell For prokaryotic host cells that do not recognize and process the native anti-ErbB3 antibody signal sequence, the signal sequence is substituted by a prokaryotic signal sequence. selected, for example, from the group of the alkaline phosphatase, penicillinase, lpp, or heat-stable enterotoxin II leaders. For yeast secretion the native signal sequence may be substituted by, e.g., the yeast invertase leader, α factor leader (including Saccharomyces and Kluyveromyces α-factor leaders), or acid phosphatase leader, the *C. albicans* glucoamylase leader, or the signal described in WO 90/13646. In mammalian cell expression, mammalian signal sequences as well as viral secretory leaders, for example, the herpes simplex gD signal, are available.

The DNA for such precursor region is ligated in reading frame to DNA encoding the anti-ErbB3 antibody.

(ii) Origin of Replication Component

Both expression and cloning vectors contain a nucleic acid sequence that enables the vector to replicate in one or more selected host cells. Generally, in cloning vectors this sequence is one that enables the vector to replicate independently of the host chromosomal DNA, and includes origins of replication or autonomously replicating sequences. Such sequences are well known for a variety of bacteria, yeast, and viruses. The origin of replication from the plasmid pBR322 is suitable for most Gram-negative bacteria, the 2 μ plasmid origin is suitable for yeast, and various viral origins (SV40, polyoma, adenovirus, VSV or BPV) are useful for cloning vectors in mammalian cells. Generally, the origin of replication component is not needed for mammalian expression vectors (the SV40 origin may typically be used only because it contains the early promoter).

(iii) Selection Gene Component

Expression and cloning vectors may contain a selection gene, also termed a selectable marker. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media, e.g., the gene encoding D-alanine racemase for *Bacilli*.

One example of a selection scheme utilizes a drug to arrest growth of a host cell. Those cells that are successfully transformed with a heterologous gene produce a protein conferring drug resistance and thus survive the selection regimen. Examples of such dominant selection use the drugs neomycin, mycophenolic acid and hygromycin.

Another example of suitable selectable markers for mammalian cells are those that enable the identification of cells competent to take up the anti-ErbB3 antibody nucleic acid, such as DHFR, thymidine kinase, metallothionein-I and -II, preferably primate metallothionein genes, adenosine deaminase, ornithine decarboxylase, etc.

For example, cells transformed with the DHFR selection gene are first identified by culturing all of the transformants in a culture medium that contains methotrexate (Mtx), a competitive antagonist of DHFR. An appropriate host cell when wild-type DHFR is employed is the Chinese hamster ovary (CHO) cell line deficient in DHFR activity.

Alternatively, host cells (particularly wild-type hosts that contain endogenous DHFR) transformed or co-transformed with DNA sequences encoding anti-ErbB3 antibody, wild-type DHFR protein, and another selectable marker such as aminoglycoside 3'-phosphotransferase (APH) can be selected by cell growth in medium containing a selection agent for the selectable marker such as an aminoglycosidic antibiotic, e.g., kanamycin, neomycin, or G418. See U.S. Pat. No. 4,965,199.

A suitable selection gene for use in yeast is the trp1 gene present in the yeast plasmid YRp7 (Stinchcomb et al., *Nature*, 282:39 (1979)). The trp1 gene provides a selection marker for a mutant strain of yeast lacking the ability to grow in tryptophan, for example, ATCC No. 44076 or PEP4-1. Jones, *Genetics*, 85:12 (1977). The presence of the trp1 lesion in the yeast host cell genome then provides an effective environment for detecting transformation by growth in the absence of tryptophan. Similarly, Leu2-deficient yeast strains (ATCC 20,622 or 38,626) are complemented by known plasmids bearing the Leu2 gene.

In addition, vectors derived from the 1.6 μm circular plasmid pKD1 can be used for transformation of *Kluyveromyces* yeasts. Alternatively, an expression system for large-scale production of recombinant calf chymosin was reported for *K. lactis*. Van den Berg, *Bio/Technology*, 8:135 (1990). Stable multi-copy expression vectors for secretion of mature recombinant human serum albumin by industrial strains of *Kluyveromyces* have also been disclosed. Fleer et al., *Bio/Technology*, 9:968-975 (1991).

(iv) Promoter Component

Expression and cloning vectors usually contain a promoter that is recognized by the host organism and is operably linked to the anti-ErbB3 antibody nucleic acid. Promoters suitable for use with prokaryotic hosts include the phoA promoter, β-lactamase and lactose promoter systems, alkaline phosphatase, a tryptophan (trp) promoter system, and hybrid promoters such as the tac promoter. However, other known bacterial promoters are suitable. Promoters for use in bacterial systems also will contain a Shine-Dalgarno (S.D.) sequence operably linked to the DNA encoding the anti-ErbB3 antibody.

Promoter sequences are known for eukaryotes. Virtually all eukaryotic genes have an AT-rich region located approximately 25 to 30 bases upstream from the site where transcription is initiated. Another sequence found 70 to 80 bases upstream from the start of transcription of many genes is a CNCAAT region where N may be any nucleotide. At the 3' end of most eukaryotic genes is an AATAAA sequence that may be the signal for addition of the poly A tail to the 3' end of the coding sequence. All of these sequences are suitably inserted into eukaryotic expression vectors.

Examples of suitable promoting sequences for use with yeast hosts include the promoters for 3-phosphoglycerate kinase or other glycolytic enzymes, such as enolase, glyceraldehyde-3-phosphate dehydrogenase, hexokinase, pyruvate decarboxylase, phospho-fructokinase, glucose-6-phosphate isomerase, 3-phosphoglycerate mutase, pyruvate kinase, triosephosphate isomerase, phosphoglucose isomerase, and glucokinase.

Other yeast promoters, which are inducible promoters having the additional advantage of transcription controlled by growth conditions, are the promoter regions for alcohol dehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization. Suitable vectors and promoters for use in yeast expression are further described in EP 73,657. Yeast enhancers also are advantageously used with yeast promoters.

Anti-ErbB3 antibody transcription from vectors in mammalian host cells is controlled, for example, by promoters obtained from the genomes of viruses such as polyoma virus, fowlpox virus, adenovirus (such as Adenovirus 2), bovine papilloma virus, avian sarcoma virus, cytomegalovirus, a retrovirus, hepatitis-B virus and most preferably Simian Virus 40 (SV40), from heterologous mammalian promoters, e.g., the actin promoter or an immunoglobulin promoter, from heat-shock promoters, provided such promoters are compatible with the host cell systems.

The early and late promoters of the SV40 virus are conveniently obtained as an SV40 restriction fragment that also contains the SV40 viral origin of replication. The immediate early promoter of the human cytomegalovirus is conveniently obtained as a HindIII E restriction fragment. A system for expressing DNA in mammalian hosts using the bovine papilloma virus as a vector is disclosed in U.S. Pat. No. 4,419,446. A modification of this system is described in U.S. Pat. No. 4,601,978. See also Reyes et al., *Nature*, 297:598-601 (1982) on expression of human β-interferon cDNA in mouse cells under the control of a thymidine kinase promoter from herpes simplex virus. Alternatively, the rous sarcoma virus long terminal repeat can be used as the promoter.

(v) Enhancer Element Component

Transcription of a DNA encoding the anti-ErbB3 antibody of this invention by higher eukaryotes is often increased by inserting an enhancer sequence into the vector. Many enhancer sequences are now known from mammalian genes (globin, elastase, albumin, α-fetoprotein, and insulin). Typically, however, one will use an enhancer from a eukaryotic cell virus. Examples include the SV40 enhancer on the late side of the replication origin (bp 100-270), the cytomegalovirus early promoter enhancer, the polyoma enhancer on the late side of the replication origin, and adenovirus enhancers. See also Yaniv, *Nature*, 297:17-18 (1982) on enhancing elements for activation of eukaryotic promoters. The enhancer may be spliced into the vector at a position 5' or 3' to the anti-ErbB3 antibody-encoding sequence, but is preferably located at a site 5' from the promoter.

(vi) Transcription Termination Component

Expression vectors used in eukaryotic host cells (yeast, fungi, insect, plant, animal, human, or nucleated cells from other multicellular organisms) will also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding anti-ErbB3 antibody. One useful transcription termination component is the bovine growth hormone polyadenylation region. See WO94/11026 and the expression vector disclosed therein.

(vii) Selection and Transformation of Host Cells

Suitable host cells for cloning or expressing the DNA in the vectors herein are the prokaryote, yeast, or higher eukaryote cells described above. Suitable prokaryotes for this purpose include eubacteria, such as Gram-negative or Gram-positive organisms, for example, Enterobacteriaceae such as *Escherichia*, e.g., *E. coli*, *Enterobacter*, *Erwinia*, *Klebsiella*, *Proteus*, *Salmonella*, e.g., *Salmonella typhimurium*, *Serratia*, e.g., *Serratia marcescans*, and *Shigella*, as well as *Bacilli* such as *B. subtilis* and *B. licheniformis* (e.g., *B. licheniformis* 41P disclosed in DD 266,710 published Apr. 12, 1989), Pseudomonas such as *P. aeruginosa*, and *Streptomyces*. One preferred *E. coli* cloning host is *E. coli* 294 (ATCC 31,446), although other strains such as *E. coli* B, *E. coli* X1776 (ATCC 31,537), and *E. coli* W3110 (ATCC 27,325) are suitable. These examples are illustrative rather than limiting.

In addition to prokaryotes, eukaryotic microbes such as filamentous fungi or yeast are suitable cloning or expression hosts for anti-ErbB3 antibody-encoding vectors. *Saccharomyces cerevisiae*, or common baker's yeast, is the most commonly used among lower eukaryotic host microorganisms. However, a number of other genera, species, and strains are commonly available and useful herein, such as *Schizosaccharomyces pombe*; *Kluyveromyces* hosts such as, e.g., *K. lactis*, *K. fragilis* (ATCC 12,424), *K. bulgaricus* (ATCC 16,045), *K. wickeramii* (ATCC 24,178), *K. waltii* (ATCC 56,500), *K. drosophilarum* (ATCC 36,906), *K. thermotolerans*, and *K. marxianus*; yarrowia (EP 402,226); *Pichia pastoris* (EP 183,070); Candida; *Trichoderma reesia* (EP 244,234); *Neurospora crassa*; *Schwanniomyces* such as *Schwanniomyces occidentalis*; and filamentous fungi such as, e.g., *Neurospora*, *Penicillium*, *Tolypocladium*, and *Aspergillus* hosts such as *A. nidulans* and *A. niger*.

Suitable host cells for the expression of glycosylated anti-ErbB3 antibody are derived from multicellular organisms. Examples of invertebrate cells include plant and insect cells. Numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melongaster* (fruitfly), and *Bombyx mori* have been identified. A variety of viral strains for transfection are publicly available, e.g., the L-1 variant of *Autographa californica* NPV and the Bm-5 strain of *Bombyx mori* NPV, and such viruses maybe used as the virus herein according to the present invention, particularly for transfection of *Spodoptera frugiperda* cells.

Plant cell cultures of cotton, corn, potato, soybean, petunia, tomato, and tobacco can also be utilized as hosts.

However, interest has been greatest in vertebrate cells, and propagation of vertebrate cells in culture (tissue culture) has become a routine procedure. Examples of useful mammalian host cell lines are monkey kidney CV1 line transformed by SV40 (COS-7, ATCC CRL 1651); human embryonic kidney line (293 or 293 cells subcloned for growth in suspension culture, Graham et al., *J. Gen Virol.*, 36:59 (1977)); baby hamster kidney cells (BHK, ATCC CCL 10); Chinese hamster ovary cells/-DHFR (CHO, Urlaub et al., *Proc. Natl. Acad. Sci. USA*, 77:4216 (1980)); mouse sertoli cells (TM4, Mather, *Biol. Reprod.*, 23:243-251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., *Annals N.Y. Acad. Sci.*, 383:44-68 (1982)); MRC 5 cells; FS4 cells; and a human hepatoma line (Hep G2).

Host cells are transformed with the above-described expression or cloning vectors for anti-ErbB3 antibody production and cultured in conventional nutrient media modified as appropriate for inducing promoters, selecting transformants, or amplifying the genes encoding the desired sequences.

(viii) Culturing the Host Cells

The host cells used to produce the anti-ErbB3 antibody of this invention may be cultured in a variety of media. Commercially available media such as Ham's F10 (Sigma), Minimal Essential Medium ((MEM), (Sigma), RPMI-1640 (Sigma), and Dulbecco's Modified Eagle's Medium ((DMEM), Sigma) are suitable for culturing the host cells. In addition, any of the media described in Ham et al. *Meth. Enz.*, 58:44 (1979), Barnes et al., *Anal. Biochem.*,102:255 (1980), U.S. Pat. Nos. 4,767,704; 4,657,866; 4,927,762; 4,560,655; or 5,122,469; WO 90/03430; WO 87/00195; or U.S. Pat. No. Re. 30,985 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as GENTAMYCIN™g), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

(ix) Purification of Anti-ErbB3 Antibody

When using recombinant techniques, the antibody can be produced intracellularly, in the periplasmic space, or directly secreted into the medium. If the antibody is produced intracellularly, as a first step, the particulate debris, either host cells or lysed fragments, is removed, for example, by centrifugation or ultrafiltration. Carter et al., *Bio/Technology* 10: 163-167 (1992) describe a procedure for isolating antibodies which are secreted to the periplasmic space of *E. coli*. Briefly, cell paste is thawed in the presence of sodium acetate (pH 3.5), EDTA, and phenylmethylsulfonylfluoride (PMSF) over about 30 min. Cell debris can be removed by centrifugation. Where the antibody is secreted into the medium, supernatants from such expression systems are generally first concentrated using a commercially available protein concentration filter, for example, an Amicon or Millipore Pellicon ultrafiltration unit. A protease inhibitor such as PMSF may be included in any of the foregoing steps to inhibit proteolysis and antibiotics may be included to prevent the growth of adventitious contaminants.

The antibody composition prepared from the cells can be purified using, for example, hydroxylapatite chromatography, gel electrophoresis, dialysis, and affinity chromatography, with affinity chromatography being the preferred purification technique. The suitability of protein A as an affinity ligand depends on the species and isotype of any immunoglobulin Fc domain that is present in the antibody. Protein A can be used to purify antibodies that are based on human γ1, γ2, or γ4 heavy chains (Lindmark et al., *J. Immunol. Meth.* 62:1-13 (1983)). Protein G is recommended for all mouse isotypes and for human γ3 (Cuss et al., *EMBO J.* 5:15671575 (1986)). The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. Where the antibody comprises a $C_H3$ domain, the Bakerbond ABX™resin (J. T. Baker, Phillipsburg, N.J.) is useful for purification. Other techniques for protein purification such as fractionation on an ion-exchange column, ethanol precipitation, Reverse Phase HPLC, chromatography on silica, chromatography on heparin Sepharose™ chromatography on an anion or cation exchange resin (such as a polyaspartic acid column), chromatofocusing, SDS-PAGE, and ammonium sulfate precipitation are also available depending on the antibody to be recovered.

Following any preliminary purification step(s), the mixture comprising the antibody of interest and contaminants may be subjected to low pH hydrophobic interaction chromatography using an elution buffer at a pH between about 2.5-4.5, preferably performed at low salt concentrations (e.g. from about 0-0.25M salt).

C. Pharmaceutical Formulations

Therapeutic formulations of the antibody are prepared for storage by mixing the antibody having the desired degree of purity with optional physiologically acceptable carriers, excipients or stabilizers (*Remington's Pharmaceutical Sciences* 16th edition, Osol, A. Ed. (1980)), in the form of lyophilized formulations or aqueous solutions. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as Tween™, Pluronics™ or polyethylene glycol (PEG).

The formulation herein may also contain more than one active compound as necessary for the particular indication being treated, preferably those with complementary activities that do not adversely affect each other. For example, it may be desirable to further provide antibodies which bind to EGFR ErbB2, ErbB4, or vascular endothelial factor (VEGF) in the one formulation Alternatively, or in addition, the composition may comprise a chemotherapeutic agent or a cytokine. Such molecules are suitably present in combination in amounts that are effective for the purpose intended.

The active ingredients may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in *Remington's Pharmaceutical Sciences* 16th edition, Osol, A. Ed. (1980).

The formulations to be used for in vivo administration must be sterile. This is readily accomplished by filtration through sterile filtration membranes.

Sustained-release preparations may be prepared. Suitable examples of sustained-release preparations include semipermeable matrices of solid hydrophobic polymers containing the antibody, which matrices are in the form of shaped articles, e.g. films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and γ ethyl-L-glutamate, non-degradable ethylene-vinyl acetate, degradable lactic acid-glycolic acid copolymers such as the Lupron Depot™(injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods. When encapsulated antibodies remain in the body for a long time, they may denature or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecular S-S bond formation through thio-disulfide interchange, stabilization may be achieved by modifying sulfhydryl residues, lyophilizing from acidic solutions, controlling moisture content, using appropriate additives, and developing specific polymer matrix compositions.

D. Non-therapeutic Uses for the Antibody

The antibodies of the invention may be used as affinity purification agents. In this process, the antibodies are immobilized on a solid phase such a Sephadex resin or filter paper, using methods well known in the art. The immobilized antibody is contacted with a sample containing the ErbB3 protein (or fragment thereof) to be purified, and thereafter the support is washed with a suitable solvent that will remove substantially all the material in the sample except the ErbB3 protein, which is bound to the immobilized antibody. Finally, the support is washed with another suitable solvent, such as glycine buffer, pH 5.0, that will release the ErbB3 protein from the antibody.

Anti-ErbB3 antibodies may also be useful in diagnostic assays for ErbB3 protein, e.g., detecting its expression in specific cells, tissues, or serum. Thus, the antibodies may be used in the diagnosis of human malignancies (see, for example, U.S. Pat. No. 5,183,884).

For diagnostic applications, the antibody typically will be labeled with a detectable moiety. Numerous labels are available which can be generally grouped into the following categories:

(a) Radioisotopes, such as $^{35}S$, $^{14}C$, $^{125}I$, $^{3}H$, and $^{131}I$. The antibody can be labeled with the radioisotope using the techniques described in *Current Protocols in Immunology*, Volumes 1 and 2, Coligen et al., Ed., Wiley-Interscience, New York, New York, Pubs., (1991) for example and radioactivity can be measured using scintillation counting.

(b) Fluorescent labels such as rare earth chelates (europium chelates) or fluorescein and its derivatives, rhodamine and its derivatives, dansyl, Lissamine, phycoerythrin and Texas Red are available. The fluorescent labels can be conjugated to the antibody using the techniques disclosed in *Current Protocols in Immunology*, supra, for example. Fluorescence can be quantified using a fluorimeter.

(c) Various enzyme-substrate labels are available and U.S. Pat. No. 4,275,149 provides a review of some of these. The enzyme generally catalyses a chemical alteration of the chromogenic substrate which can be measured using various techniques. For example, the enzyme may catalyze a color change in a substrate, which can be measured spectrophotometrically. Alternatively, the enzyme may alter the fluorescence or chemiluminescence of the substrate. Techniques for quantifying a change in fluorescence are described above. The chemiluminescent substrate becomes electronically excited by a chemical reaction and may then emit light which can be measured (using a chemiluminometer, for example) or donates energy to a fluorescent acceptor. Examples of enzymatic labels include luciferases (e.g., firefly luciferase and bacterial luciferase; U.S. Pat. No. 4,737,456), luciferin, 2,3-dihydrophthalazinediones, malate dehydrogenase, urease, peroxidase such as horseradish peroxidase (HRPO), alkaline phosphatase, β-galactosidase, glucoamylase, lysozyme, saccharide oxidases (e.g., glucose oxidase, galactose oxidase, and glucose-6-phosphate dehydrogenase), heterocyclic oxidases (such as uricase and xanthine oxidase), lactoperoxidase, microperoxidase, and the like. Techniques for conjugating enzymes to antibodies are described in O'Sullivan et al., Methods for the Preparation of Enzyme-Antibody Conjugates for use in Enzyme Immunoassay, in *Methods in Enzym*. (ed J. Langone & H. Van Vunakis), Academic press, New York, 73: 147-166 (1981).

Examples of enzyme-substrate combinations include, for example:

(i) Horseradish peroxidase (HRPO) with hydrogen peroxidase as a substrate, wherein the hydrogen peroxidase oxidizes a dye precursor (e.g. orthophenylene diamine (OPD) or 3,3',5,5'-tetramethyl benzidine hydrochloride (TMB));

(ii) alkaline phosphatase (AP) with para-Nitrophenyl phosphate as chromogenic substrate; and (iii) β-D-galactosidase (β-D-Gal) with a chromogenic substrate (e.g. p-nitrophenyl-β-D-galactosidase) or fluorogenic substrate 4-methylumbelliferyl-β-D-galactosidase.

Numerous other enzyme-substrate combinations are available to those skilled in the art. For a general review of these, see U.S. Pat. Nos. 4,275,149 and 4,318,980.

Sometimes, the label is indirectly conjugated with the antibody. The skilled artisan will be aware of various techniques for achieving this. For example, the antibody can be conjugated with biotin and any of the three broad categories of labels mentioned above can be conjugated with avidin, or vice versa. Biotin binds selectively to avidin and thus, the label can be conjugated with the antibody in this indirect manner. Alternatively, to achieve indirect conjugation of the label with the antibody, the antibody is conjugated with a small hapten (e.g. digoxin) and one of the different types of labels mentioned above is conjugated with an anti-hapten antibody (e.g. anti-digoxin antibody). Thus, indirect conjugation of the label with the antibody can be achieved.

In another embodiment of the invention, the anti-ErbB3 antibody need not be labeled, and the presence thereof can be detected using a labeled antibody which binds to the ErbB3 antibody.

The antibodies of the present invention may be employed in any known assay method, such as competitive binding assays, direct and indirect sandwich assays, and immunoprecipitation assays. Zola, *Monoclonal Antibodies: A Manual of Techniques*, pp. 147-158 (CRC Press, Inc., 1987).

Competitive binding assays rely on the ability of a labeled standard to compete with the test sample analyte for binding with a limited amount of antibody. The amount of ErbB3 protein in the test sample is inversely proportional to the amount of standard that becomes bound to the antibodies. To facilitate determining the amount of standard that becomes bound, the antibodies generally are insolubilized before or after the competition, so that the standard and analyte that are bound to the antibodies may conveniently be separated from the standard and analyte which remain unbound.

Sandwich assays involve the use of two antibodies, each capable of binding to a different immunogenic portion, or epitope, of the protein to be detected. In a sandwich assay, the test sample analyte is bound by a first antibody which is immobilized on a solid support, and thereafter a second antibody binds to the analyte, thus forming an insoluble three-part complex. See, e.g., U.S. Pat. No. 4,376,110. The second antibody may itself be labeled with a detectable moiety (direct sandwich assays) or may be measured using an anti-immunoglobulin antibody that is labeled with a detectable moiety (indirect sandwich assay). For example, one type of sandwich assay is an ELISA assay, in which case the detectable moiety is an enzyme.

For immunohistochemistry, the tumor sample may be fresh or frozen or may be embedded in paraffin and fixed with a preservative such as formalin, for example.

The antibodies may also be used for in vivo diagnostic assays. Generally, the antibody is labelled with a radionuclide (such as $^{111}$In, $^{99}$Tc, $^{14}$C, 131I, $^{125}$I, $^3$H, $^{32}$P or $^{35}$S) so that the tumor can be localized using immunoscintiography.

E. Diagnostic Kits

As a matter of convenience, the antibody of the present invention can be provided in a kit, i.e., a packaged combination of reagents in predetermined amounts with instructions for performing the diagnostic assay. Where the antibody is labelled with an enzyme, the kit will include substrates and cofactors required by the enzyme (e.g. a substrate precursor which provides the detectable chromophore or fluorophore). In addition, other additives may be included such as stabilizers, buffers (e.g. a block buffer or lysis buffer) and the like. The relative amounts of the various reagents may be varied widely to provide for concentrations in solution of the reagents which substantially optimize the sensitivity of the assay. Particularly, the reagents may be provided as dry powders, usually lyophilized, including excipients which on dissolution will provide a reagent solution having the appropriate concentration.

F. Therapeutic Uses for the Antibody

It is contemplated that the anti-ErbB3 antibody of the present invention may be used to treat conditions in which excessive activation of the ErbB2-ErbB3 complex is occurring, particularly where such activation is mediated by a heregulin polypeptide. Exemplary conditions or disorders to be treated with the ErbB3 antibody include benign or malignant tumors (e.g. renal, liver, kidney, bladder, breast, gastric, ovarian, colorectal, prostate, pancreatic, ling, vulval, thyroid, hepatic carcinomas; sarcomas; glioblastomas; and various head and neck tumors); leukemias and lymphoid malignancies; other disorders such as neuronal, glial, astrocytal, hypothalamic and other glandular, macrophagal, epithelial, stromal and blastocoelic disorders; and inflammatory, angiogenic and immunologic disorders.

The antibodies of the invention are administered to a mammal, preferably a human, in accord with known methods, such as intravenous administration as a bolus or by continuous infusion over a period of time, by intramuscular, intraperitoneal, intracerobrospinal, subcutaneous, intra-articular, intrasynovial, intrathecal, oral, topical, or inhalation routes. Intravenous administration of the antibody is preferred.

Other therapeutic regimens may be combined with the administration of the anti-ErbB3 antibodies of the instant invention. For example, the patient to be treated with the antibodies disclosed herein may also receive radiation therapy. Alternatively, or in addition, a chemotherapeutic agent may be administered to the patient. Preparation and dosing schedules for such chemotherapeutic agents may be used according to manufacturers' instructions or as determined empirically by the skilled practitioner. Preparation and dosing schedules for such chemotherapy are also described in Chemotherapy Service Ed., M. C. Perry, Williams & Wilkins, Baltimore, Md. (1992). The chemotherapeutic agent may precede, or follow administration of the antibody or may be given simultaneously therewith.

It may be desirable to also administer antibodies against other tumor associated antigens, such as antibodies which bind to the EGFR, ErbB2, ErbB4, or vascular endothelial factor (VEGF). Two or more anti-ErbB3 antibodies may be co-administered to the patient. Alternatively, or in addition one or more cytokines may be administered to the patient.

For the prevention or treatment of disease, the appropriate dosage of antibody will depend on the type of disease to be treated, as defined above, the severity and course of the disease, whether the antibody is administered for preventive or therapeutic purposes, previous therapy, the patient's clinical history and response to the antibody, and the discretion of the attending physician. The antibody is suitably administered to the patient at one time or over a series of treatments.

Depending on the type and severity of the disease, about 1 µg/kg to 15 mg/kg (e.g. 0.1-20 mg/kg) of antibody is an initial candidate dosage for administration to the patient, whether, for example, by one or more separate administrations, or by continuous infusion. A typical daily dosage might range from about 1 µg/kg to 100 mg/kg or more, depending on the factors mentioned above. For repeated administrations over several days or longer, depending on the condition, the treatment is sustained until a desired suppression of disease symptoms occurs. However, other dosage regimens may be useful. The progress of this therapy is easily monitored by conventional techniques and assays.

G. Articles of Manufacture

In another embodiment of the invention, an article of manufacture containing materials useful for the treatment of the disorders described above is provided. The article of manufacture comprises a container and a label. Suitable containers include, for example, bottles, vials, syringes, and test tubes. The containers may be formed from a variety of materials such as glass or plastic. The container holds a composition which is effective for treating the condition and may have a sterile access port (for example the container may be an intravenous solution bag or a vial having a stopper pierceable by a hypodermic injection needle). The active agent in the composition is the anti-ErbB3 antibody. The label on, or associated with, the container indicates that the composition is used for treating the condition of choice. The article of manufacture may further comprise a second container comprising a pharmaceutically-acceptable buffer, such as phosphate-buffered saline, Ringer's solution and dextrose solution. It may further include other materials desirable from a commercial and user standpoint, including other buffers, diluents, filters, needles, syringes, and package inserts with instructions for use.

H. Deposit of Materials

The following hybridoma cell line has been deposited with the American Type Culture Collection, 10801 University Blvd., Manassas, Va. 20110-2209 (ATCC):

| Hybridoma/Antibody Designation | ATCC No. | Deposit Date |
| --- | --- | --- |
| 8B8 | HB12070 | March 22, 1996 |

This deposit was made under the provisions of the Budapest Treaty on the International Recognition of the Deposit of Microorganisms for the Purpose of Patent Procedure and the Regulations thereunder (Budapest Treaty). This assures maintenance of a viable culture for 30 years from the date of deposit. The cell line will be made available by ATCC under the terms of the Budapest Treaty, and subject to an agreement between Genentech, Inc. and ATCC, which assures (a) that access to the culture will be available during pendency of the patent application to one determined by the Commissioner to be entitled thereto under 37 CFR § 1.14 and 35 USC § 122, and (b) that all restrictions on the availability to the public of the culture so deposited will be irrevocably removed upon the granting of the patent.

The assignee of the present application has agreed that if the culture on deposit should die or be lost or destroyed when cultivated under suitable conditions, it will be promptly replaced on notification with a viable specimen of the same culture. Availability of the deposited cell line is not to be construed as a license to practice the invention in contravention of the rights granted under the authority of any government in accordance with its patent laws.

The foregoing written specification is considered to be sufficient to enable one skilled in the art to practice the invention. The present invention is not to be limited in scope by the culture deposited, since the deposited embodiment is intended as a single illustration of one aspect of the invention and any culture that is functionally equivalent is within the scope of this invention The deposit of material herein does not constitute an admission that the written description herein contained is inadequate to enable the practice of any aspect of the invention, including the best mode thereof, nor is it to be construed as limiting the scope of the claims to the specific illustration that it represents. Indeed, various modifications of the invention in addition to those shown and described herein will become apparent to those skilled in the art from the foregoing description and fall within the scope of the appended claims.

The following examples are offered by way of illustration and not by way of limitation. The disclosures of all citations in the specification are expressly incorporated herein by reference.

EXAMPLE

Production of Anti-ErbB3 Antibodies

This example describes the production of the anti-ErbB3 antibodies having the characteristics described herein.

Materials and Methods

Cell Lines. The human myeloid leukemia cell line K562 (which lacks class I subfamily receptor protein tyrosine kinases as determined by Northern blotting) and human ovarian carcinoma cell line Caov3 were obtained from the American Type Culture Collection (Rockville, Md.). Both were cultured in RPMI 1640 medium supplemented with 10% fetal bovine serum, 2 mM glutamine, 100 µ/mL penicillin, 100 µg/mL streptomycin, and 10 mM HEPES ("growth medium").

Stable Transfection of K562 Cells. The K562 cell line was transfected and ErbB3 expressing clones were selected for. Briefly, erbB3 cDNA was subcloned into the pcDNA-3 mammalian cell expression vector (Invitrogen) and introduced into K562 cells by electroporation (1180 mF, 350 V). Transfected cells were cultured in growth medium containing 0.8 mg/mL G418. Resistant clones were obtained by limiting dilution and tested for ErbB3 expression by Western blot and heregulin (HRG) binding assays. The ErbB3 expressing clone 4E9H3 was used in the experiments described in this report. Phorbol ester stimulation was found to significantly enhance ErbB3 expression in the K562 transfectants. Therefore, the 4E9H3 cells were placed in growth medium containing 10 ng/mL phorbol-12-myristate acetate (PMA) overnight prior to use in the various assays described below.

Antibodies. Monoclonal antibodies specific for ErbB3 protein were generated against a recombinant fragment of the receptor corresponding to the extracellular domain (ECD) thereof fused at its amino terminus to the herpes simplex virus type I (HSV I) glycoprotein D (gD) epitope for the monoclonal antibody 5B6. The coding sequence for the signal sequence of ErbB3 was replaced with a sequence encoding amino acids 1-53 of the gD polypeptide. Amino acids 1-25 encode the signal sequence of gD while amino acids 26-53 contain an epitope for the monoclonal antibody 5B6. See WO 95/14776. The resulting construct, gD.ErB3.ECD, was purified using an anti-gD antibody affinity column. Immunizations were performed as follows. Female Balb/c mice (Charles River) were initially injected via footpad with 5 µg of gD.ErbB3.ECD in 100 µl RIBI's™ adjuvant (Ribi ImmunochemResearch, Inc., Hamilton, Mont.). The animals were boosted 2 times with 5 µg of gD.ErbB3.ECD in their footpad every two weeks followed by a final footpad injection of 5 µg of gD.ErbB3.ECD. Three days after the last immunization, popliteal lymph nodes were removed and a single cell suspension was prepared for PEG fusion.

Monoclonal antibodies were purified and tested by immobilized and solution phase ELISA for cross-reactivity with ErbB2 and ErbB4. For the immobilized ELISA, 1 µg/ml of ErbB2.ECD, gD.ErbB3.ECD or gD.ErbB4.ECD was used to coat a 96 well microtiter plate overnight. Anti-ErbB3 Mab at 1 µg/ml was added and incubated for 1 hour at room temperature (RT) washed and followed by goat anti-mouse (gam) IgG conjugated to HRPO. The ELISA was developed and read at 490 nm. For the solution phase ELISA, 1 µg/ml of gam IgG (Fc specific) was used to coat a 96 well microtiter plate overnight. Anti-ErbB3 Mab at 1 µg/ml was added and incubated for 1 hour at RT, washed and followed by biotinylated ErbB2.ECD, gD.ErbB3.ECD or gD.ErbB4.ECD. This reaction was incubated for 1 hour at RT, washed and followed by HRPO strepavidin. The ELISA was developed and read at 490 nm. In this assay, none of the anti-ErbB3 antibodies cross-reacted with ErbB2 or ErbB4.

Fab fragments of the 3-8D6 antibody were generated by papain digestion. Undigested IgG and Fc fragments were removed by protein A affinity chromatography followed by gel filtration chromatography. No IgG was detectable in the Fab pool by SDS-PAGE and by a Western blot probed with an Fc specific antibody.

HRG Binding Assays. All HRG binding experiments were carried out using the EGF-like domain of the β1 isoform, i.e. HRGβ1$_{177\text{-}244}$ (Sliwkowski et al., *J. Biol. Chem.* 269: 14661-5 (1994)). The ErbB3 antibody panel was screened for an effect on HRG binding by incubating $5.0\times10^4$ 4E9H3 cells with 100 pM $^{125}$I-HRG overnight at 0° C., in the absence (control) or presence of 100 nM anti-ErbB3 antibody. Irrelevant IgGs were used as negative controls. The cells were harvested and rapidly washed with ice cold assay buffer (RPMI medium containing 10 mM HEPES, pH=7.2) in a 96 well filtration device (Millipore). The filters were then removed and counted.

For the antibody dose-response experiments, 4E9H3 cells were incubated with 100 pM $^{125}$I-HRG in the presence of increasing concentrations of antibody. HRG affinity measurements were determined in the absence (control) or presence of either 100 nM antibody or Fab fragment. These experiments were carried out in a competitive inhibition format with increasing amounts of unlabeled HRG and a fixed concentration (35 pM) of $^{125}$I-HRG. For the control experiment (no antibody) $1\times10^5$ 4E9H3 cells were used for each sample. Due to limitations in the dynamic range of the assay, the number of 4E9H3 cells used for binding in the presence of either the antibody or the Fab was reduced to $2.5\times10^4$ cells per sample.

Antibody reduction of HRG stimulated phosphorylation. Caov3 cells, which naturally express ErbB2 and ErbB3, were pre-incubated with 250 nM anti-ErbB3 antibody 3-8D6, Fab fragments of this antibody, or buffer (control), for 60 minutes at room temperature. The anti-ErbB2 antibody, 2C4 (Fendly et al., *Cancer Res.*, 50:1550-1558 (1990)), which was previously shown to block HRG stimulated phosphorylation of ErbB2 was included as a positive control. The cells were then stimulated with HRG at a final concentration of 10 nM for 8 minutes at room temperature, or left unstimulated. The reaction was stopped by removing the supernatants and dissolving the cells in SDS sample buffer. The lysates were then run on SDS-PAGE. Western blots of the gels were probed with anti-phosphotyrosine conjugated to horseradish peroxidase (Transduction Labs), and the blots were visualized using a chemiluminescent substrate (Amersham). The blots were scanned with a reflectance scanning densitometer as described in Holmes et al., *Science*, 256:1205-1210 (1992).

Antibody reduction of ErbB2-ErbB3 protein complex formation. Caov3 cells were pre-incubated with buffer (control), 250 nM anti-ErbB3 antibody 3-8D6, or Fab fragments of this antibody, or the anti-ErbB2 antibody (2C4) for 60 minutes at room temperature, then treated with 10 nM HRG or control buffer for 10 minutes. The cells were lysed in 25 mM Tris, pH=7.5, 150 mM NaCl, 1 mM EDTA, 1.0% Triton X-100™, 1.0% CHAPS, 10% v/v glycerol, containing 0.2 mM PMSF, 50 mTU/mL aprotinin, and 10 mM leupeptin ("lysis buffer"), and the crude lysates were centrifuged briefly to remove insoluble material. Supernatants were incubated with 3E8, a monoclonal antibody specific for ErbB2 (Fendly et al., *Cancer Res.*, 50:1550-1558 (1990)), covalently coupled to an insoluble support (Affi Prep-10™, Bio-Rad). The incubation was carried out overnight at 4° C. The immunoprecipitates were washed twice with ice cold lysis buffer, re-suspended in a minimal volume of SDS sample buffer, and run on SDS-PAGE. Western blots of the gels were then probed with a polyclonal anti-ErbB3 (Santa Cruz Biotech). The blots were scanned with a reflectance scanning densitometer as described in Holmes et al., *Science*, 256:1205-1210 (1992). After visualization with the ECL chemiluminescent substrate, the blots were stripped and re-probed with a polyclonal anti-ErbB2 (Santa Cruz Biotech). A duplicate plot probed with anti-ErbB2 showed that equal amounts of ErbB2 were immunoprecipitated from each sample.

Results

A panel of monoclonal antibodies directed against the extracellular domain of ErbB3 were evaluated for their ability to affect HRG binding to ErbB3. The initial screen was carried out by incubating each of the purified antibodies at a final concentration of 100 nM with 4E9H3 cells in the presence of $^{125}$I-HRG. 4E9H3 cells are ErbB3 transfectants of the human myeloid leukemia cell line K562. The K562 cell line does not express endogenous ErbB receptors or HRG. Therefore, heregulin binding to 4E9H3 cells occurs exclusively through ErbB3. After incubating the samples overnight on ice, cell associated counts were measured. As shown in FIG. 1, two of the anti-ErbB3 monoclonal antibodies (2F9 and 3E9) reduced the amount of $^{125}$I-HRG bound to 4E9H3 cells relative to control (no antibody). However, several others significantly enhanced ligand binding. These results suggested that these anti-ErbB3 antibodies were able to increase the affinity for HRG binding and/or increase the availability of HRG binding sites. To further characterize the influence of these antibodies on HRG binding to ErbB3, dose-response experiments were performed using the 3-8D6 antibody that increased HRG binding. 4E9H3 cells were incubated with 100 pM of $^{125}$I-HRG in the presence of increasing concentrations of the 3-8D6 antibody. Cell associated counts were then measured after an overnight incubation on ice. The results are shown in FIG. 2 as plots of cell associated counts versus antibody concentrations. There is a correlation between increased HRG binding and increasing antibody concentration. Heregulin binding reached saturation between 10 and 100 nM IgG. The $EC_{50}$ value for the 3-8D6 antibody was 722 pM. No decrease in the dose-response curves at high antibody concentrations were observed for either antibody.

Scatchard analysis of HRG binding was determined in the presence of these antibodies and the results are shown in Table 1.

TABLE 1

| Data Set | $K_d$ | Sites/Cell |
| --- | --- | --- |
| Control | $1.2 \times 10^{-9}$ | $3.6 \times 10^5$ |
| MAb 3-8D6 | $2.1 \times 10^{-10}$ | $2.4 \times 10^5$ |
| FAb 3-8D6 | $2.8 \times 10^{-10}$ | $2.9 \times 10^5$ |

In the absence of the antibody, a Kd of 1200 pM was measured for HRG binding to ErbB3, which is in agreement with a previously measured affinity measurement of HRG binding to ErbB3. The number of binding sites per cell was determined to be 36,000. In the presence of the antibody, 3-8D6, the measured binding constant for HRG binding is significantly increased to 210 pM. However, the number of HRG binding sites is not increased in the presence of 3-8D6.

To determine whether the increase in ErbB3 ligand binding affinity was dependent on the antibody being divalent, HRG binding experiments were performed in the presence of 100 nM of a Fab fragment prepared by papain digestion of the 3-8D6 antibody. Fab fragments used for these experiments were purified by Protein A affinity chromatography and by gel filtration chromatography. No intact IgG was detected in this purified preparation by SDS-PAGE. As shown in FIG. 3, binding of HRG in the presence of the intact antibody or the resulting Fab is nearly identical. Scatchard analysis of these data yield a dissociation constant for HRG binding in the presence of Fab of 280 pM and the number of receptors per cell determined from this experiment was also essentially the same as that of the control. These data are consistent with those presented in FIG. 2, where the dose response curves with the intact antibodies showed a plateau rather than a bell-shaped curve at higher antibody concentration, where univalent antibody binding might be occurring. Without being bound by any theory, these data suggest that the alteration in HRG binding observed in the presence of these antibodies does not require a divalent antibody.

The effect of the 3-8D6 antibody in a receptor tyrosine phosphorylation assay, using the ovarian tumor cell line Caov3 which co-expresses ErbB2 and ErbB3 was next examined. Cells were stimulated with 10 nM HRG following a 60 minute pre-incubation with either the 3-8D6 antibody (at 250 nM) or buffer (control). Whole cell lysates were analyzed on a Western blot probed with anti-phosphotyrosine. HRG treatment did not stimulate phosphorylation in 4E9H3 cells. Treatment of 4E9H3 cells with the 3-8D6 antibody did not induce phosphorylation of ErbB3 by itself nor did it have any effect on tyrosine phosphorylation in Caov3 cells. A marked tyrosine phosphorylation signal was detected on a protein with a molecular size~180 kDa following HRG stimulation. Treatment of Caov3 cells with 2C4, an antibody specific for ErbB2, was able to block the HRG-mediated tyrosine phosphorylation signal. When cells were treated with the anti-ErbB3 antibody, 3-8D6, prior to HRG stimulation, tyrosine phosphorylation was also decreased. By scanning densitometry of the anti-phosphotyrosine blots of whole cell lysates, it was observed that 3-8D6 inhibits the phosphotyrosine signal at 180-185 kDa by about 80% (range 76-84%). This signal is contributed by tyrosine phosphate residues on both ErbB3 and ErbB2. Treatment of Caov3 cells with the Fab fragments prepared from the 3-8D6 antibody, also reduced the HRG stimulated phosphorylation of the 180 kDa band relative to control. However, the inhibitory activity of the Fab was slightly less potent than the intact antibody.

The 3-8D6 antibody-mediated increase in receptor affinity on cells which express ErbB3 alone is analogous to the increase in affinity associated with co-expression of ErbB2 with ErbB3. Moreover, this antibody blocks the HRG stimulated ErbB2 kinase activity in cells which express both receptors. To determine whether the anti-ErbB3 antibody competes directly with ErbB2 for binding to ErbB3, a series of co-immunoprecipitation experiments were performed using Caov3 cells. Cells were pre-incubated with either antibody, or buffer (control) and then treated with 10 nM HRG for 10 minutes. Lysates of the cells were then immunoprecipitated with a monoclonal antibody against ErbB2. Immunoprecipitates were then analyzed by Western blot for the presence of ErbB3. The results of these experiments indicated that ErbB3 was present in the ErbB2 immunoprecipitate of the HRG stimulated cell lysate, but not in the immunoprecipitate of unstimulated lysate. These data suggests that HRG drives the formation of an ErbB2-ErbB3 complex in Caov3 cells. ErbB3 was not detectable in the immunoprecipitate of the sample treated with the anti-ErbB2 monoclonal antibody, 2C4. A significant diminution in the ErbB3 signal was observed when the cells were pre-incubated with the 3-8D6 antibody or its resulting Fab prior to HRG stimulation. These data indicate that the 3-8D6 antibody inhibits the formation of a ErbB2-ErbB3 complex following HRG treatment. Scanning densitometry of the anti-ErbB3 Western blots of anti-ErbB2 immunoprecipitates revealed that the anti-ErbB3 signal (which indicates the number of ErbB2-ErbB3 complexes present) is also diminished by 3-8D6 by about 80% (range 71-90%). When duplicate blots were probed with anti-ErbB2, equivalent amounts of ErbB2 were present in all lanes.

What is claimed is:

1. An isolated nucleic acid encoding an antibody comprising the complementarity determining regions of the 8B8 antibody (ATCC HB-12070).

2. The nucleic acid of claim 1, wherein the antibody is a monoclonal antibody.

3. The nucleic acid of claim 2, wherein the antibody is humanized.

4. A vector comprising the isolated nucleic acid of claim 1.

5. A host cell comprising the isolated nucleic acid of claim 1.

6. A method for making an antibody comprising culturing the host cell of claim 5 so that the nucleic acid is expressed and recovering the antibody from the host cell culture.

7. The method of claim 6 further comprising conjugating the recovered antibody with a cytotoxic agent or enzyme.

* * * * *